US009345728B2

(12) United States Patent
Petit et al.

(10) Patent No.: US 9,345,728 B2
(45) Date of Patent: *May 24, 2016

(54) NON-REPLICATING PROBIOTIC MICRO-ORGANISMS PROTECT CHILDREN AGAINST GASTROINTESTINAL INFECTIONS

(75) Inventors: Valerie Petit, Thonon-les-Bains (FR); Clara Lucia Garcia-Rodenas, Forel (CH); Monique Julita, Prilly (CH); Annick Mercenier, Bussigny (CH); Guenolee Prioult, Bern (CH); Sophie Nutten, Palezieux-Village (CH)

(73) Assignee: Nestec S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/884,524

(22) PCT Filed: Nov. 9, 2011

(86) PCT No.: PCT/EP2011/069693
§ 371 (c)(1),
(2), (4) Date: May 9, 2013

(87) PCT Pub. No.: WO2012/062781
PCT Pub. Date: May 18, 2012

(65) Prior Publication Data
US 2013/0224254 A1  Aug. 29, 2013

(30) Foreign Application Priority Data

Nov. 11, 2010 (EP) .................................. 10190847

(51) Int. Cl.
| A61K 39/116 | (2006.01) |
| A61K 39/00 | (2006.01) |
| A01N 63/00 | (2006.01) |
| A01N 65/00 | (2009.01) |
| A61K 35/741 | (2015.01) |
| A61K 35/74 | (2015.01) |
| A61K 35/742 | (2015.01) |
| A61K 35/744 | (2015.01) |
| A61K 35/745 | (2015.01) |
| A61K 35/747 | (2015.01) |
| A61K 35/12 | (2015.01) |
| A61K 38/00 | (2006.01) |

(52) U.S. Cl.
CPC ............... *A61K 35/741* (2013.01); *A61K 35/74* (2013.01); *A61K 35/742* (2013.01); *A61K 35/744* (2013.01); *A61K 35/745* (2013.01); *A61K 35/747* (2013.01); *A61K 35/12* (2013.01); *A61K 38/00* (2013.01); *A61K 39/116* (2013.01)

(58) Field of Classification Search
CPC ..... A61K 39/116; A61K 38/00; A61K 35/74; A61K 35/12
See application file for complete search history.

(56) References Cited

U.S. PATENT DOCUMENTS

| 7,648,270 | B2 * | 1/2010 | Faour et al. ................... 374/178 |
| 8,021,656 | B2 * | 9/2011 | Corthesy-Theulaz et al. ......................... 424/93.45 |
| 8,603,492 | B2 * | 12/2013 | Mercenier et al. ......... 424/282.1 |
| 8,802,077 | B2 * | 8/2014 | Petit et al. .................... 424/93.4 |
| 2005/0180962 | A1 * | 8/2005 | Raz et al. .................... 424/93.45 |
| 2007/0172547 | A1 * | 7/2007 | Kume et al. ..................... 426/36 |
| 2010/0254956 | A1 * | 10/2010 | Arulampalam et al. ... 424/93.45 |
| 2013/0028877 | A1 * | 1/2013 | Petit et al. .................. 424/93.45 |
| 2013/0224167 | A1 * | 8/2013 | Petit et al. .................. 424/93.44 |
| 2013/0260440 | A1 * | 10/2013 | Petit et al. ..................... 435/245 |

FOREIGN PATENT DOCUMENTS

| EP | 1384483 A1 * | 1/2004 |
| EP | 2251022 | 11/2010 |
| EP | 2449890 | 5/2012 |
| EP | 2449887 | * 9/2012 |
| EP | 2449889 | * 9/2012 |
| EP | 2449891 | * 9/2012 |
| WO | WO9806411 | 2/1998 |
| WO | WO2004069156 | 8/2004 |
| WO | WO2008106373 | 9/2008 |
| WO | WO2008153377 | 12/2008 |

OTHER PUBLICATIONS

Gastrointestinal Tract Infections, Chapter 20, pp. 253-286; accessed on Oct. 21, 2013.*
Sonnenborn et al., Microbial Ecology in Health and Disease, 2009; 21: 122-158.*
Butel, Medecine et maladies infectieuses, 2014: 1-8.*
Kaila, Minna, et al. "Viable versus inactivated lactobacillus strain GG in acute rotavirus diarrhoea." Archives of disease in childhood 72.1 (1995): 51-53.

(Continued)

*Primary Examiner* — Gary Nickol
*Assistant Examiner* — Lakia Tongue
(74) *Attorney, Agent, or Firm* — K&L Gates LLP

(57) ABSTRACT

The present invention relates to non-replicating probiotic micro-organisms and their health benefits. In particular, the present invention provides a means to help parents to protect their children from gastro-intestinal infections, in particular diarrhea. One embodiment of the present invention relates to a composition comprising non-replicating probiotic micro-organisms for use in the prevention or treatment of gastrointestinal infections in children.

12 Claims, 14 Drawing Sheets

(56) References Cited

OTHER PUBLICATIONS

Simakachorn, Nipat, et al. "Clinical evaluation of the addition of lyophilized, heat-killed Lactobacillus acidophilus LB to oral rehydration therapy in the treatment of acute diarrhea in children." Journal of Pediatric Gastroenterology and Nutrition 30.1 (2000): 68-72.

Ostad, S. N., et al. "Live and heat-inactivated lactobacilli from feces inhibit *Salmonella typhi* and *Escherichia coli* adherence to Caco-2 cells." Folia microbiologica 54.2 (2009): 157-160.

European Office Action for European Application No. 11784625.3 dated May 27, 2014 (4 pages).

Usenko D.V. "Efficiency of a Fermented Milk Product Comprising Lactobacillus casei DN-114001, in the case of H. pylori infection in children" Lechashchyi vrach, 2007. No. 7—online—www.ivrach.ru/2007/07/4535415, 4 pages.

Russian Office Action for Application No. 2013126602 dated Jun. 3, 2015—2 pages.

Moore et al., "Interleukin-10," Annu. Rev. Immunol., 1993, vol. 11, pp. 165-190.

Adams et al., "The probiotic paradox: live and dead cells are biological response modifiers," Nutrition Research Reviews, 2010, vol. 23, pp. 37-46.

Kataria et al., "Probiotic microbes: do they need to be alive to be benficial?" Nutrition Reviews, vol. 67(9), pp. 546-550.

European Search Report in Application No. 11784625.3, dated Apr. 1, 2016, 6 pages.

* cited by examiner

NON-REPLICATING PROBIOTIC MICRO-ORGANISMS PROTECT CHILDREN AGAINST GASTROINTESTINAL INFECTIONS

CROSS REFERENCE TO RELATED APPLICATIONS

The present application is a National Stage of International Application No. PCT/EP2011/069693, filed on Nov. 9, 2011, which claims priority to European Patent Application No. 10190847.3, filed Nov. 11, 2010, the entire contents of which are being incorporated herein by reference.

The present invention relates to non-replicating probiotic micro-organisms and their health benefits. In particular, the present invention provides a means to help parents to protect their children from gastro-intestinal infections, in particular diarrhea. One embodiment of the present invention relates to a composition comprising non-replicating probiotic micro-organisms for use in the prevention or treatment of gastrointestinal infections in children.

Organisms that produce lactic acid as a major metabolic component have been known for a long time. These bacteria may be found in milk or in milk processing factories, respectively, living or decaying plants but also in the intestine of man and animals. These microorganisms, summarized under the term "lactic acid bacteria", represent a rather inhomogeneous group and comprise e.g. the genera *Lactococcus, Lactobacillus, Streptococcus, Bifidobacterium, Pediococcus* etc.

Lactic acid bacteria have been utilized as fermenting agents for the preservations of food taking benefit of a low pH and the action of fermentation products generated during the fermentative activity thereof to inhibit the growth of spoilage bacteria. In addition, lactic acid bacteria have also been used for preparing from milk a variety of different foodstuff such as cheese, yogurt and other fermented dairy products. Quite recently, lactic acid bacteria have attracted a great deal of attention in that some strains have been found to exhibit valuable properties to man and animals upon ingestion. In particular, specific strains of *Lactobacillus* or *Bifidobacterium* have been found to be able to colonize the intestinal mucosa and to assist in the maintenance of the well-being of man and animal.

In this respect, EP 0 768 375 discloses specific strains of the genus *Bifidobacterium*, that are capable to become implanted in the intestinal flora and may adhere to intestinal cells. These Bifidobacteria are reported to assist in immunomodulation, being capable to competitively exclude adhesion of pathogenic bacteria to intestinal cells, thus assisting in the maintenance of the individual's health.

Research has also focused on the potential use of lactic acid bacteria as probiotic agents. Probiotics are considered to be viable microbial preparations which promote the individual's health by preserving the natural microflora in the intestine. Probiotics are deemed to attach to the intestine's mucosa, colonize the intestinal tract and likewise prevent attachment of harmful microorganisms thereon. A crucial prerequisite for their action resides in that they have to reach the gut's mucosa in a proper and viable form and do not get destroyed in the upper part of the gastrointestinal tract, especially by the influence of the low pH prevailing in the stomach.

Meanwhile, research work is in part aimed at the provision of additional probiotics bacterial strains that exhibit new properties beneficial for man and/or animals, such as pets.

U.S. Pat. No. 6,998,119 B1 pertains in this respect to the use of the non-pathogenic *Bifidobacterium* CNCM I-2168 for preparing a carrier for the treatment or prophylaxis of diarrhea brought about by rotaviruses.

US 2005260170 A1 describes that *Bifidobacterium longum* CNCM I-2169 and *Bifidobacterium longum* CNCM I-2170 have been shown to prevent colonization of intestinal cells by bacteria bringing about diarrhea, such as pathogenic *E. coli*, e.g. enteropathogenic *E. coli* (EPPC), or *salmonella*, e.g. *Salmonella typhimuriurm*.

Gastrointestinal infections, such as diarrhea for example, are very uncomfortable and may even be accompanied by fever, stomach ache, and vomiting. They may last for about one to two weeks, and—usually—uncomplicated cases will go away without treatment.

Antidiarrheal medications are available but should usually be avoided, in particular in children, unless otherwise recommended by a doctor.

Hence it would be desirable to have available a composition that helps parents to protect their children against diarrhea. The composition should be easy to prepare and its activity should remain to be high, even though a product might be stored for longer times. The composition should allow to treat or prevent gastrointestinal infections safely without side effects. The time diarrhea will last should be reduced and/or the time it takes to recover from diarrhea should be reduced. Also the risk of getting diarrhea should be reduced.

Hence it was the objective of the present invention to provide the art with a composition that addresses one or more of the needs expressed above.

The present inventors were surprised to see that they could achieve this objective by the subject matter of the independent claim. The dependant claims further develop the idea of the present invention.

Accordingly, the present invention relates to a composition comprising non-replicating probiotic micro-organisms for use in the prevention or treatment of gastrointestinal infections in children.

The present invention also relates to the use of non-replicating probiotic micro-organisms in the preparation of a composition to treat or prevent gastrointestinal infections in children.

Children may be human or animal children. Animal children comprise in particular pets, e.g. dogs and cats.

A human or an animal is considered a child until adulthood is reached.

For humans, children are up to 18 years old. Infants are children under the age of 12 months.

"Non-replicating" probiotic micro-organisms include probiotic bacteria which have been heat treated. This includes micro-organisms that are inactivated, dead, non-viable and/or present as fragments such as DNA, metabolites, cytoplasmic compounds, and/or cell wall materials.

"Non-replicating" means that no viable cells and/or colony forming units can be detected by classical plating methods. Such classical plating methods are summarized in the microbiology book: James Monroe Jay, Martin J. Loessner, David A. Golden. 2005. Modern food microbiology. 7th edition, Springer Science, New York, N.Y. 790 p. Typically, the absence of viable cells can be shown as follows: no visible colony on agar plates or no increasing turbidity in liquid growth medium after inoculation with different concentrations of bacterial preparations ('non replicating' samples) and incubation under appropriate conditions (aerobic and/or anaerobic atmosphere for at least 24 h).

Probiotics are defined for the purpose of the present invention as "Microbial cell preparations or components of microbial cells with a beneficial effect on the health or well-being of the host." (Salminen S, Ouwehand A. Benno Y. et al "Probiotics: how should they be defined" Trends Food Sci. Technol. 1999:10 107-10).

The possibility to use non-replicating probiotic micro-organisms offers several advantages. In severely immuno-compromised infants or young children, the use of live probiotics may be limited in exceptional cases due to a potential risk to develop bacteremia. Non-replicating probiotics may be used without any problem.

Additionally, the provision of non-replicating probiotic micro-organisms allows the hot reconstitution while retaining health benefits.

The composition of the present invention may be any kind of composition suitable for administration to humans or pets. Consequently, the composition may be a food product, a pet food product, a nutraceutical, a food supplement, a powdered nutritional composition, a food additive, or a drink.

The gastrointestinal infection may be diarrhea. Diarrhea may be an acute viral gastroenteritis or an inflammatory acute diarrhea, for example.

As gastrointestinal infections are usually associated with discomfort and sometimes with embarrassment, there is a need to protect children against gastrointestinal infections.

The inventors were surprised to see that, e.g., in terms of an immune boosting effect and/or in terms of an anti-inflammatory effect non-replicating probiotic microorganisms may even be more effective than replicating probiotic microorganisms.

Additionally, non-replicating heat-treated La1 (NCC533, deposit number CNCM I-1225) induced defensin expression strongly. Defensins are one of the most important classes of antimicrobial peptides in humans. Defensins are produced by epithelial cells of the lung, skin, oral cavity, genitourinary, respiratory and gastrointestinal tract. Among these, there is the family of β-defensins including the defensin 1 (hBD1) and 2 (hBD2). For example, it was found that heat-treated *L. johnsonii* (La1, NCC 533, deposit number CNCM I-1225) up-regulates hBD1 more strongly than its live counterpart. HBD1 displays antibacterial activity against a broad spectrum of bacteria including *E. coli* and *Pseudomonas aeruginosa, H. pylori* (Nuding, S., et al., 2009, Microbes. Infect. 11:384-393) and also against yeasts such as *Candida albicans* (O'Neil, D. A. 2003, Mol. Immunol 40:445-450) and viruses (human immunodeficiency virus) (Kota, S. Et al., 2008, J. Biol. Chem. 283:22417-22429). Thus, these antimicrobial peptides will reinforce the mucosal barrier and consequently limit bacterial adherence and invasion.

Consequently, the composition of the present invention may be for use in protecting children from gastrointestinal infections.

In particular, the composition of the present invention will allow parents to protect their children from gastrointestinal infections.

The composition of the present invention may also be for use in strengthening a child's ability to fight gastrointestinal infections. This is in particular important, since an active lifestyle of children is very important for their development, but also involves contact with many possible sources of infections. Strong defensive mechanisms against unwanted infections will support their wellbeing.

Consequently, the composition in accordance with the present invention may also be for use in helping children to get gastrointestinal infections less often. The likelihood with which children will get gastrointestinal infections may be reduced by at least 10%, at least 25%, at least 30%, or preferably at least 50%.

Improved anti-inflammatory properties, improved immune boosting effects of the compositions of the present invention and/or an upregulated defensin expression by the composition of the present invention will reinforce defence mechanisms resulting in fewer gastrointestinal infections.

The composition of the present invention may also be for use in the reduction of time gastrointestinal infections will last. For example, the time gastrointestinal infections, such as diarrhea, will last may be reduced by at least 10%, at least 25%, at least 30%, or preferably at least 50%.

In children antidiarrheal medications are usually not recommended unless otherwise indicated by medical personnel. The non-replicating probiotics of the present invention offer a safe and natural alternative to such antidiarrheal medications.

The compositions in accordance with the present invention may also be for use in helping children to recover from gastrointestinal infections faster. After a gastrointestinal infection is overcome, an organism is typically still somewhat weak and needs to be adapted to normal nutrition carefully. The composition of the present invention may be used to speed up this adaptation phase significantly. For example, the time it takes children to recover from gastrointestinal infections may be reduced by at least 10%, at least 25%, at least 30%, or preferably at least 50%.

The composition of the present invention may further contain prebiotics. Prebiotics may support the growth of probiotics before they are rendered non-replicating. "Prebiotic" means non-digestible food substances that promote the growth of health beneficial micro-organisms and/or probiotics in the intestines. They are not broken down in the stomach and/or upper intestine or absorbed in the GI tract of the person ingesting them, but they are fermented by the gastrointestinal microbiota and/or by probiotics. Prebiotics are for example defined by Glenn R. Gibson and Marcel B. Roberfroid, Dietary Modulation of the Human Colonic Microbiota: Introducing the Concept of Prebiotics, J. Nutr. 1995 125: 1401-1412.

The prebiotics that may be used in accordance with the present invention are not particularly limited and include all food substances that promote the growth of probiotics or health beneficial micro-organisms in the intestines. Preferably, they may be selected from the group consisting of oligosaccharides, optionally containing fructose, galactose, mannose; dietary fibers, in particular soluble fibers, soy fibers; inulin; or mixtures thereof. Preferred prebiotics are fructo-oligosaccharides (FOS), galacto-oligosaccharides (GOS), isomalto-oligosaccharides (IMO), xylo-oligosaccharides (XOS), arabino-xylo oligosaccharides (AXOS), mannan-oligosaccharides (MOS), oligosaccharides of soy, glycosylsucrose (GS), lactosucrose (LS), lactulose (LA), palatinose-oligosaccharides (PAO), malto-oligosaccharides, gums and/or hydrolysates thereof, pectins and/or hydrolysates thereof. For example, the compositions may contain oligofructose, inulin or a combination thereof.

The composition according to the present invention may comprise non replicating probiotic micro-organisms in any effective amount, for example in an amount corresponding to about $10^6$ to $10^{12}$ cfu/g dry weight.

The compositions of the present invention comprise non-replicating probiotic micro-organisms in an amount sufficient to at least partially produce a health benefit. An amount adequate to accomplish this is defined as "a therapeutically effective dose". Amounts effective for this purpose will depend on a number of factors known to those of skill in the art such as the weight and general health state of the child, and on the effect of the food matrix.

In prophylactic applications, compositions according to the invention are administered to a person susceptible to or otherwise at risk of a disorder in an amount that is sufficient to at least partially reduce the risk of developing that disorder. Such an amount is defined to be "a prophylactic effective dose". Again, the precise amounts depend on a number of factors such as the child's state of health and weight, and on the effect of the food matrix.

Those skilled in the art will be able to adjust the therapeutically effective dose and/or the prophylactic effective dose appropriately.

In general the composition of the present invention contains non-replicating probiotic micro-organisms in a therapeutically effective dose and/or in a prophylactic effective dose.

Typically, the therapeutically effective dose and/or the prophylactic effective dose is in the range of about 0.005 mg-1000 mg non-replicating, probiotic micro-organisms per daily dose.

In terms of numerical amounts, the "short-time high temperature" treated non-replicating micro-organisms may be present in the composition in an amount corresponding to between $10^4$ and $10^{12}$ equivalent cfu/g of the dry composition. Obviously, non-replicating micro-organisms do not form colonies, consequently, this term is to be understood as the amount of non replicating micro-organisms that is obtained from $10^4$ and $10^{12}$ cfu/g replicating bacteria. This includes micro-organisms that are inactivated, non-viable or dead or present as fragments such as DNA or cell wall or cytoplasmic compounds. In other words, the quantity of micro-organisms which the composition contains is expressed in terms of the colony forming ability (cfu) of that quantity of micro-organisms as if all the micro-organisms were alive irrespective of whether they are, in fact, non replicating, such as inactivated or dead, fragmented or a mixture of any or all of these states.

Preferably the non-replicating micro-organisms are present in an amount equivalent to between $10^4$ to $10^9$ cfu/g of dry composition, even more preferably in an amount equivalent to between $10^5$ and $10^9$ cfu/g of dry composition.

The probiotics may be rendered non-replicating by any method that is known in the art.

The technologies available today to render probiotic strains non-replicating are usually heat-treatment, γ-irradiation, UV light or the use of chemical agents (formalin, paraformaldehyde).

It would be preferred to use a technique to render probiotics non-replicating that is relatively easy to apply under industrial circumstances in the food industry.

Most products on the market today that contain probiotics are heat treated during their production. It would hence be convenient, to be able to heat treat probiotics either together with the produced product or at least in a similar way, while the probiotics retain or improve their beneficial properties or even gain a new beneficial property for the consumer.

However, inactivation of probiotic micro-organisms by heat treatments is associated in the literature generally with an at least partial loss of probiotic activity.

The present inventors have now surprisingly found, that rendering probiotic micro-organisms non-replicating, e.g., by heat treatment, does not result in the loss of probiotic health benefits, but—to the contrary—may enhance existing health benefits and even generate new health benefits.

Hence, one embodiment of the present invention is a composition wherein the non-replicating probiotic micro-organisms were rendered non-replicating by a heat-treatment.

Such a heat treatment may be carried out at at least 71.5° C. for at least 1 second.

Long-term heat treatments or short-term heat treatments may be used.

In industrial scales today usually short term heat treatments, such as UHT-like heat treatments are preferred. This kind of heat treatment reduces bacterial loads, and reduces the processing time, thereby reducing the spoiling of nutrients.

The inventors demonstrate for the first time that probiotics micro-organisms, heat treated at high temperatures for short times exhibit anti-inflammatory immune profiles regardless of their initial properties. In particular either a new anti-inflammatory profile is developed or an existing anti-inflammatory profile is enhanced by this heat treatment.

It is therefore now possible to generate non replicating probiotic micro-organisms with anti-inflammatory immune profiles by using specific heat treatment parameters that correspond to typical industrially applicable heat treatments, even if live counterparts are not anti-inflammatory strains.

Hence, for example, the heat treatment may be a high temperature treatment at about 71.5-150° C. for about 1-120 seconds. The high temperature treatment may be a high temperature/short time (HTST) treatment or a ultra-high temperature (UHT) treatment.

The probiotic micro-organisms may be subjected to a high temperature treatment at about 71.5-150° C. for a short term of about 1-120 seconds.

More preferred the micro-organisms may be subjected to a high temperature treatment at about 90-140° C., for example 90°-120° C., for a short term of about 1-30 seconds.

This high temperature treatment renders the micro-organisms at least in part non-replicating.

The high temperature treatment may be carried out at normal atmospheric pressure but may be also carried out under high pressure. Typical pressure ranges are form 1 to 50 bar, preferably from 1-10 bar, even more preferred from 2 to 5 bar. Obviously, it is preferred if the probiotics are heat treated in a medium that is either liquid or solid, when the heat is applied. An ideal pressure to be applied will therefore depend on the nature of the composition which the micro-organisms are provided in and on the temperature used.

The high temperature treatment may be carried out in the temperature range of about 71.5-150° C., preferably of about 90-120° C., even more preferred of about 120-140° C.

The high temperature treatment may be carried out for a short term of about 1-120 seconds, preferably, of about 1-30 seconds, even more preferred for about 5-15 seconds.

This given time frame refers to the time the probiotic micro-organisms are subjected to the given temperature. Note, that depending on the nature and amount of the composition the micro-organisms are provided in and depending on the architecture of the heating apparatus used, the time of heat application may differ.

Typically, however, the composition of the present invention and/or the micro-organisms are treated by a high temperature short time (HTST) treatment, flash pasteurization or a ultra high temperature (UHT) treatment.

A UHT treatment is Ultra-high temperature processing or a ultra-heat treatment (both abbreviated UHT) involving the at least partial sterilization of a composition by heating it for a short time, around 1-10 seconds, at a temperature exceeding 135° C. (275° F.), which is the temperature required to kill bacterial spores in milk. For example, processing milk in this way using temperatures exceeding 135° C. permits a decrease of bacterial load in the necessary holding time (to 2-5 s) enabling a continuous flow operation.

There are two main types of UHT systems: the direct and indirect systems. In the direct system, products are treated by steam injection or steam infusion, whereas in the indirect system, products are heat treated using plate heat exchanger, tubular heat exchanger or scraped surface heat exchanger. Combinations of UHT systems may be applied at any step or at multiple steps in the process of product preparation.

A HTST treatment is defined as follows (High Temperature/Short Time): Pasteurization method designed to achieve a 5-log reduction, killing 99.9999% of the number of viable micro-organisms in milk. This is considered adequate for destroying almost all yeasts, molds and common spoilage bacteria and also ensure adequate destruction of common pathogenic heat resistant organisms. In the HTST process milk is heated to 71.7° C. (161° F.) for 15-20 seconds.

Flash pasteurization is a method of heat pasteurization of perishable beverages like fruit and vegetable juices, beer and dairy products. It is done prior to filling into containers in order to kill spoilage micro-organisms, to make the products safer and extend their shelf life. The liquid moves in controlled continuous flow while subjected to temperatures of 71.5° C. (160° F.) to 74° C. (165° F.) for about 15 to 30 seconds.

For the purpose of the present invention the term "short time high temperature treatment" shall include high-temperature short time (HTST) treatments, UHT treatments, and flash pasteurization, for example.

Since such a heat treatment provides non-replicating probiotics with an improved anti-inflammatory profile, the composition of the present invention may be for use in the prevention or treatment of inflammatory disorders.

If long term heat treatments are used to render the probiotic micro-organisms non-replicating, such a heat treatment may be carried out in the temperature range of about 70-150° C. for about 3 minutes-2 hours, preferably in the range of 80-140° C. from 5 minutes-40 minutes.

While the prior art generally teaches that bacteria rendered non-replicating by long-term heat-treatments are usually less efficient than live cells in terms of exerting their probiotic properties, the present inventors were able to demonstrate that heat-treated probiotics are superior in stimulating the immune system compared to their live counterparts.

The present invention relates also to a composition comprising probiotic micro-organisms that were rendered non-replicating by a heat treatment at at least about 70° C. for at least about 3 minutes.

The immune boosting effects of non-replicating probiotics were confirmed by in vitro immunoprofiling. The in vitro model used uses cytokine profiling from human Peripheral Blood Mononuclear Cells (PBMCs) and is well accepted in the art as standard model for tests of immunomodulating compounds (Schultz et al., 2003, Journal of Dairy Research 70, 165-173; Taylor et al., 2006, Clinical and Experimental Allergy, 36, 1227-1235; Kekkonen et al., 2008, World Journal of Gastroenterology, 14, 1192-1203)

The in vitro PBMC assay has been used by several authors/research teams for example to classify probiotics according to their immune profile, i.e. their anti- or pro-inflammatory characteristics (Kekkonen et al., 2008, World Journal of Gastroenterology, 14, 1192-1203). For example, this assay has been shown to allow prediction of an anti-inflammatory effect of probiotic candidates in mouse models of intestinal colitis (Foligne, B., et al., 2007, World J. Gastroenterol. 13:236-243). Moreover, this assay is regularly used as read-out in clinical trials and was shown to lead to results coherent with the clinical outcomes (Schultz et al., 2003, Journal of Dairy Research 70, 165-173; Taylor et al., 2006, Clinical and Experimental Allergy, 36, 1227-1235).

Allergic diseases have steadily increased over the past decades and they are currently considered as epidemics by WHO. In a general way, allergy is considered to result from an imbalance between the Th1 and Th2 responses of the immune system leading to a strong bias towards the production of Th2 mediators. Therefore, allergy can be mitigated, down-regulated or prevented by restoring an appropriate balance between the Th1 and Th2 arms of the immune system. This implies the necessity to reduce the Th2 responses or to enhance, at least transiently, the Th1 responses. The latter would be characteristic of an immune boost response, often accompanied by for example higher levels of IFNγ, TNF-α and IL-12. (Kekkonen et al., 2008, World Journal of Gastroenterology, 14, 1192-1203; Viljanen M. et al., 2005, Allergy, 60, 494-500)

The composition of the present invention allows it hence to treat or prevent disorders that are related to a compromised immune defence.

The composition described in the present invention allows it also to enhance a response to vaccines, in particular to oral vaccines.

Any amount of non-replicating micro-organisms will be effective. However, it is generally preferred, if at least 90%, preferably, at least 95%, more preferably at least 98%, most preferably at least 99%, ideally at least 99.9%, most ideally all of the probiotics are non-replicating.

In one embodiment of the present invention all microorganisms are non-replicating.

Consequently, in the composition of the present invention at least 90%, preferably, at least 95%, more preferably at least 98%, most preferably at least 99%, ideally at least 99.9%, most ideally all of the probiotics are non-replicating.

All probiotic micro-organisms may be used for the purpose of the present invention.

For example, the probiotic micro-organisms may be selected from the group consisting of bifidobacteria, lactobacilli, propionibacteria, or combinations thereof, for example *Bifidobacterium longum, Bifidobacterium lactis, Bifidobacterium animalis, Bifidobacterium breve, Bifidobacterium infantis, Bifidobacterium adolescentis, Lactobacillus acidophilus, Lactobacillus casei, Lactobacillus paracasei, Lactobacillus salivarius, Lactobacillus reuteri, Lactobacillus rhamnosus, Lactobacillus johnsonii, Lactobacillus plantarum, Lactobacillus fermentum, Lactococcus lactis, Streptococcus thermophilus, Lactococcus lactis, Lactococcus diacetylactis, Lactococcus cremoris, Lactobacillus bulgaricus, Lactobacillus helveticus, Lactobacillus delbrueckii, Escherichia coli* and/or mixtures thereof.

The composition in accordance with the present invention may, for example, comprise probiotic micro-organisms selected from the group consisting of *Bifidobacterium longum* NCC 3001, *Bifidobacterium longum* NCC 2705, *Bifidobacterium breve* NCC 2950, *Bifidobacterium lactis* NCC 2818, *Lactobacillus johnsonii* La1, *Lactobacillus paracasei* NCC 2461, *Lactobacillus rhamnosus* NCC 4007, *Lactobacillus reuteri* DSM17938, *Lactobacillus reuteri* ATCC55730, *Streptococcus thermophilus* NCC 2019, *Streptococcus thermophilus* NCC 2059, *Lactobacillus casei* NCC 4006, *Lactobacillus acidophilus* NCC 3009, *Lactobacillus casei* ACA-DC 6002 (NCC 1825), *Escherichia coli* Nissle, *Lactobacillus bulgaricus* NCC 15, *Lactococcus lactis* NCC 2287, or combinations thereof.

All these strains were either deposited under the Budapest treaty and/or are commercially available.

The strains have been deposited under the Budapest treaty as follows:

*Bifidobacterium longum* NCC 3001: ATCC BAA-999 (deposited on Jan. 29, 2001 at the Institut Pasteur, 28 rue du Docteur Roux, F-75024 Paris Cedex 15, France)

*Bifidobacterium longum* NCC 2705: CNCM I-2618

*Bifidobacterium breve* NCC 2950: CNCM I-3865 (deposited on Nov. 15, 2007 at the Institut Pasteur, 28 rue du Docteur Roux, F-75024 Paris Cedex 15, France)

*Bifidobacterium lactis* NCC 2818: CNCM I-3446 (deposited on Jun. 7, 2005 at the Institut Pasteur, 28 rue du Docteur Roux, F-75024 Paris Cedex 15, France)

*Lactobacillus paracasei* NCC 2461: CNCM I-2116 (deposited on Jan. 12, 1999 at the Institut Pasteur, 28 rue du Docteur Roux, F-75024 Paris Cedex 15, France)

*Lactobacillus rhamnosus* NCC 4007: CGMCC 1.3724 (deposited in October 2004 at the China General Microbiological Culture Collection Center, Chinese Academy of Sciences, P.O. Box 2714, Beijing, China 100080)

*Streptococcus thermophilus* NCC 2019: CNCM I-1422 (deposited on May 18, 1994 at the Institut Pasteur, 28 rue du Docteur Roux, F-75024 Paris Cedex 15, France)

*Streptococcus thermophilus* NCC 2059: CNCM I-4153 (deposited on Apr. 24, 2009 at the Institut Pasteur, 28 rue du Docteur Roux, F-75024 Paris Cedex 15, France)

*Lactococcus lactis* NCC 2287: CNCM I-4154 (deposited on Apr. 24, 2009 at the Institut Pasteur, 28 rue du Docteur Roux, F-75024 Paris Cedex 15, France)

*Lactobacillus casei* NCC 4006: CNCM I-1518 (deposited on Jun. 12, 2008 at the Institut Pasteur, 28 rue du Docteur Roux, F-75024 Paris Cedex 15, France)

*Lactobacillus casei* NCC 1825: ACA-DC 6002

*Lactobacillus acidophilus* NCC 3009: ATCC 700396

*Lactobacillus bulgaricus* NCC 15: CNCM I-1198 (deposited on Apr. 2, 1992 at the Institut Pasteur, 28 rue du Docteur Roux, F-75024 Paris Cedex 15, France)

*Lactobacillus johnsonii* La1: CNCM I-1225 (deposited on Jun. 30, 1992 at the Institut Pasteur, 28 rue du Docteur Roux, F-75024 Paris Cedex 15, France)

*Lactobacillus reuteri* DSM17938: DSM17938

*Lactobacillus reuteri* ATCC55730: ATCC55730

*Escherichia coli* Nissle 1917: DSM 6601

Strains named ATCC were deposited with the ATCC Patent Depository, 10801 University Blvd., Manassas, Va. 20110, USA.

Strains named CNCM were deposited with the COLLECTION NATIONALE DE CULTURES DE MICROORGANISMES (CNCM), 25 rue du Docteur Roux, F-75724 PARIS Cedex 15, France.

Strains named CGMCC were deposited with the China General Microbiological Culture Collection Center, Institute of Microbiology, Chinese Academy of Sciences, Zhongguancun, P.O. Box 2714, Beijing 100080, China.

Strains named ACA-DC were deposited with the Greek Coordinated Collections of Microorganisms, Dairy Laboratory, Department of Food Science and Technology, Agricultural University of Athens, 75, Iera odos, Botanikos, Athens, 118 55, Greece.

Strains named DSM were deposited with the DSMZ-Deutsche Sammlung von Mikroorganismen and Zellkulturen GmbH, Inhoffenstr. 7 B, 38124 Braunschweig, GERMANY.

Those skilled in the art will understand that they can freely combine all features of the present invention described herein, without departing from the scope of the invention as disclosed.

Further advantages and features of the present invention are apparent from the following Examples and Figures.

FIGS. 1 A and B show the enhancement of the anti-inflammatory immune profiles of probiotics treated with "short-time high temperatures".

FIG. 2 shows non anti-inflammatory probiotic strains that become anti-inflammatory, i.e. that exhibit pronounced anti-inflammatory immune profiles in vitro after being treated with "short-time high temperatures".

FIGS. 3 A and B show probiotic strains in use in commercially available products that exhibit enhanced or new anti-inflammatory immune profiles in vitro after being treated with "short-time high temperatures".

FIGS. 4 A and B show dairy starter strains (i.e. Lc1 starter strains) that exhibits enhanced or new anti-inflammatory immune profiles in vitro upon heat treatment at high temperatures.

FIG. 5 shows a non anti-inflammatory probiotic strain that exhibits anti-inflammatory immune profiles in vitro after being treated with HTST treatments.

FIG. 6: Principal Component Analysis on PBMC data (IL-12p40, IFN-γ, TNF-α, IL-10) generated with probiotic and dairy starter strains in their live and heat treated (140° C. for 15 second) forms. Each dot represents one strain either live or heat treated identified by its NCC number or name.

Figure 9:
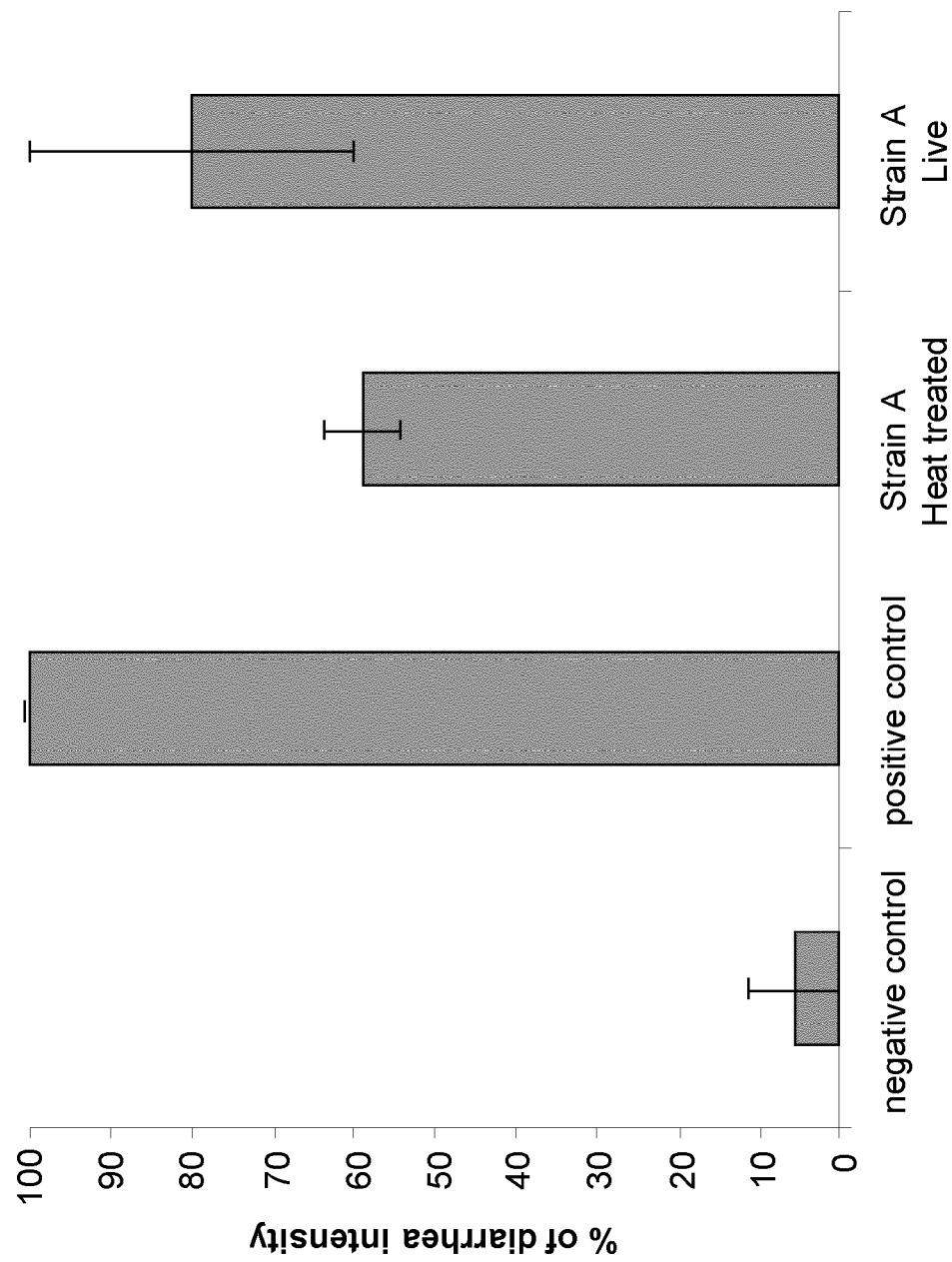

FIG. 9 shows the percentage of diarrhea intensity observed in OVA-sensitized mice challenged with saline (negative control), OVA-sensitized mice challenged with OVA (positive control) and OVA-sensitized mice challenged with OVA and treated with heat-treated or live *Bifidobacterium breve* NCC2950. Results are displayed as the percentage of diarrhea intensity (Mean±SEM calculated from 4 independent experiments) with 100% of diarrhea intensity corresponding to the symptoms developed in the positive control (sensitized and challenged by the allergen) group.

Figure 10:
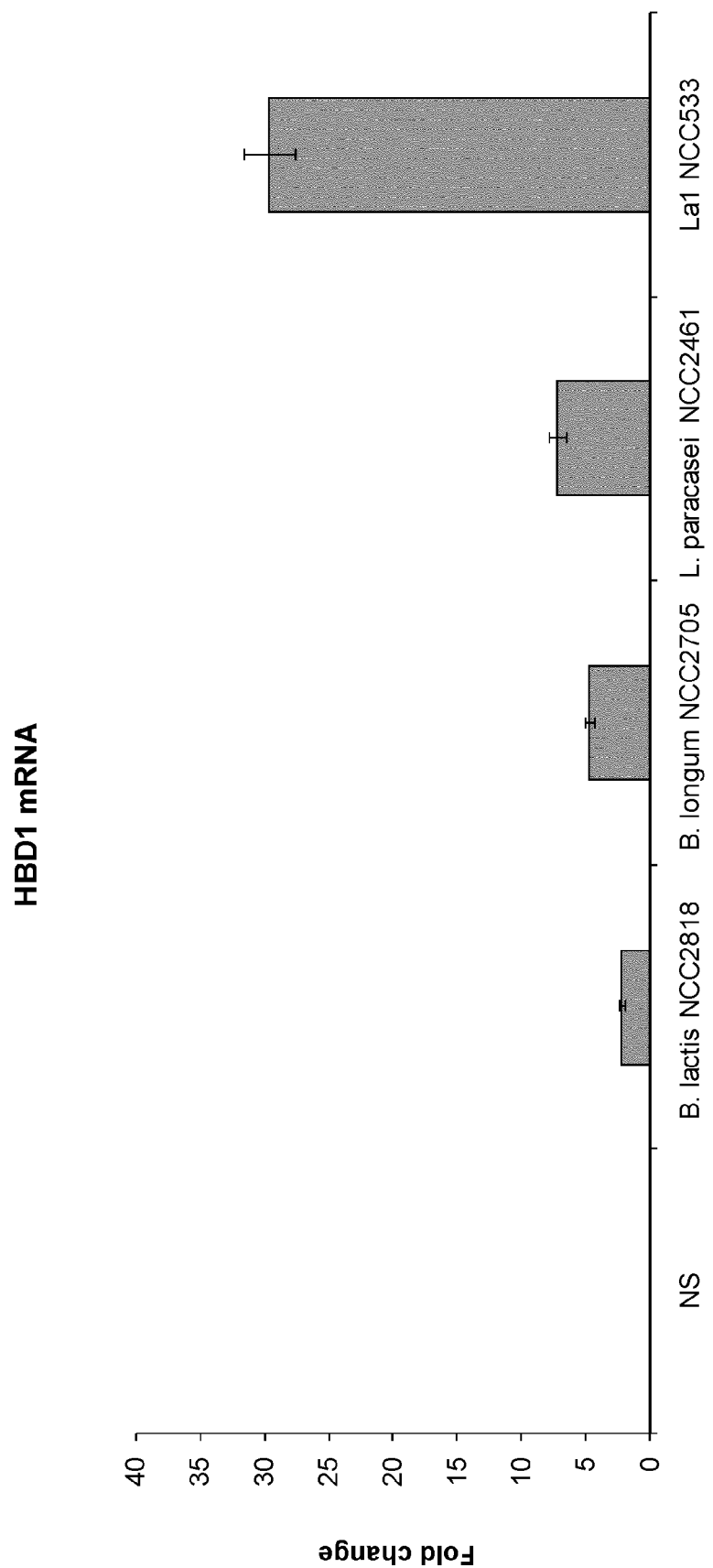

FIG. 10 shows that heat treated La1 (NCC533, deposit number CNCM I-1225) at 120° C.-15 sec strongly induces hBD1 mRNA in intestinal epithelial cells in vitro compared with other heat-treated strains. T84 cells were incubated for 4 h with the heat-treated strains. Gene expression of hBD1 was analyzed by real-time PCR. The bars represent the means±sem normalized to basal expression of non stimulated cells.

Figure 11:
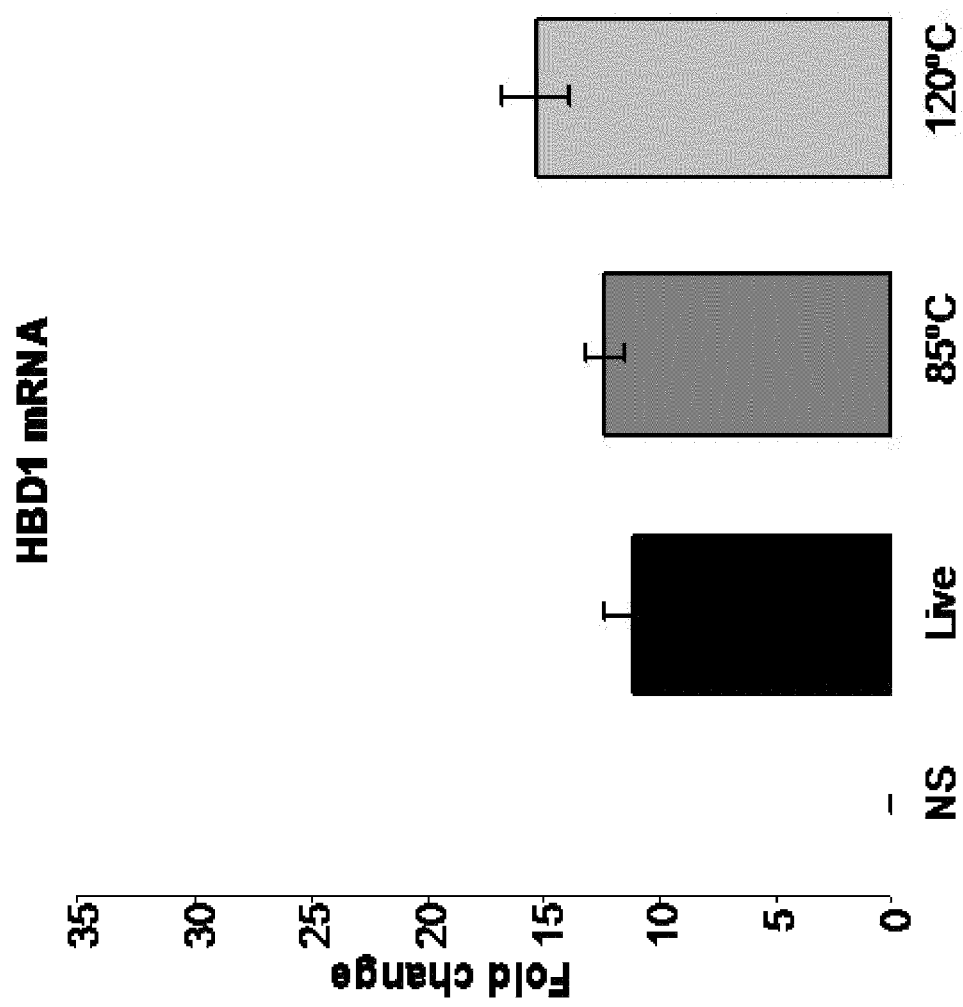

FIG. 11 shows that a high temperature and short time treatment of La1 (NCC533, deposit number CNCM I-1225) tends to be the best to induce hBD1 mRNA expression. T84 cells were stimulated for 4 h with the live and heat-treated La1 (NCC533, deposit number CNCM I-1225) at 120° C.-15 sec or 85° C.-20 min. Gene expression of hBD1 was analyzed by real-time PCR. The bars represent the means±sem normalized to basal expression of non stimulated cells.

EXAMPLE 1

Methodology

Bacterial Preparations:

The health benefits delivered by live probiotics on the host immune system are generally considered to be strain specific. Probiotics inducing high levels of IL-10 and/or inducing low levels of pro-inflammatory cytokines in vitro (PBMC assay) have been shown to be potent anti-inflammatory strains in vivo (Foligné, B., et al., 2007, World J. Gastroenterol. 13:236-243).

Several probiotic strains were used to investigate the anti-inflammatory properties of heat treated probiotics. These were *Bifidobacterium longum* NCC 3001, *Bifidobacterium longum* NCC 2705, *Bifidobacterium breve* NCC 2950, *Bifidobacterium lactis* NCC 2818, *Lactobacillus paracasei* NCC 2461, *Lactobacillus rhamnosus* NCC 4007, *Lactobacillus casei* NCC 4006, *Lactobacillus acidophilus* NCC 3009, *Lactobacillus casei* ACA-DC 6002 (NCC 1825), and *Escherichia coli* Nissle. Several starter culture strains including some strains commercially used to produce Nestlé Lc1 fermented products were also tested: *Streptococcus thermophilus* NCC 2019, *Streptococcus thermophilus* NCC 2059, *Lactobacillus bulgaricus* NCC 15 and *Lactococcus lactis* NCC 2287.

Bacterial cells were cultivated in conditions optimized for each strain in 5-15 L bioreactors. All typical bacterial growth media are usable. Such media are known to those skilled in the art. When pH was adjusted to 5.5, 30% base solution (either NaOH or $Ca(OH)_2$) was added continuously. When adequate, anaerobic conditions were maintained by gassing headspace with $CO_2$. *E. coli* was cultivated under standard aerobic conditions.

Bacterial cells were collected by centrifugation (5,000×g, 4° C.) and re-suspended in phosphate buffer saline (PBS) in adequate volumes in order to reach a final concentration of around $10^9$-$10^{10}$ cfu/ml. Part of the preparation was frozen at −80° C. with 15% glycerol. Another part of the cells was heat treated by:

Ultra High Temperature: 140° C. for 15 sec; by indirect steam injection

High Temperature Short Time (HTST): 74° C., 90° C. and 120° C. for 15 sec by indirect steam injection Long Time Low Temperature (85° C., 20 min) in water bath Upon heat treatment, samples were kept frozen at −80° C. until use.

In Vitro Immunoprofiling of Bacterial Preparations:

The immune profiles of live and heat treated bacterial preparations (i.e. the capacity to induce secretion of specific cytokines from human blood cells in vitro) were assessed. Human peripheral blood mononuclear cells (PBMCs) were isolated from blood filters. After separation by cell density gradient, mononuclear cells were collected and washed twice with Hank's balanced salt solution. Cells were then resuspended in Iscove's Modified Dulbecco's Medium (IMDM, Sigma) supplemented with 10% foetal calf serum (Bioconcept, Paris, france), 1% L-glutamine (Sigma), 1% penicillin/streptomycin (Sigma) and 0.1% gentamycin (Sigma). PBMCs ($7\times10^5$ cells/well) were then incubated with live and heat treated bacteria (equivalent $7\times10^6$ cfu/well) in 48 well plates for 36 h. The effects of live and heat treated bacteria were tested on PBMCs from 8 individual donors splitted into two separated experiments. After 36 h incubation, culture plates were frozen and kept at −20° C. until cytokine measurement. Cytokine profiling was performed in parallel (i.e. in the same experiment on the same batch of PBMCs) for live bacteria and their heat-treated counterparts.

Levels of cytokines (IFN-γ, IL-12p40, TNF-α and IL-10) in cell culture supernatants after 36 h incubation were determined by ELISA (R&D DuoSet Human IL-10, BD OptEIA Human IL12p40, BD OptEIA Human TNFα, BD OptEIA Human IFN-γ) following manufacturer's instructions. IFN-γ, IL-12p40 and TNF-α are pro-inflammatory cytokines, whereas IL-10 is a potent anti-inflammatory mediator. Results are expressed as means (pg/ml)+/− SEM of 4 individual donors and are representative of two individual experiments performed with 4 donors each. The ratio IL-12p40/IL-10 is calculated for each strain as a predictive value of in vivo anti-inflammatory effect (Foligné, B., et al., 2007, World J. Gastroenterol. 13:236-243).

Numerical cytokine values (pg/ml) determined by ELISA (see above) for each strain were transferred into BioNumerics v5.10 software (Applied Maths, Sint-Martens-Latem, Belgium). A Principal Component Analysis (PCA, dimensioning technique) was performed on this set of data. Subtraction of the averages over the characters and division by the variances over the characters were included in this analysis.

Results

Figure 4A:
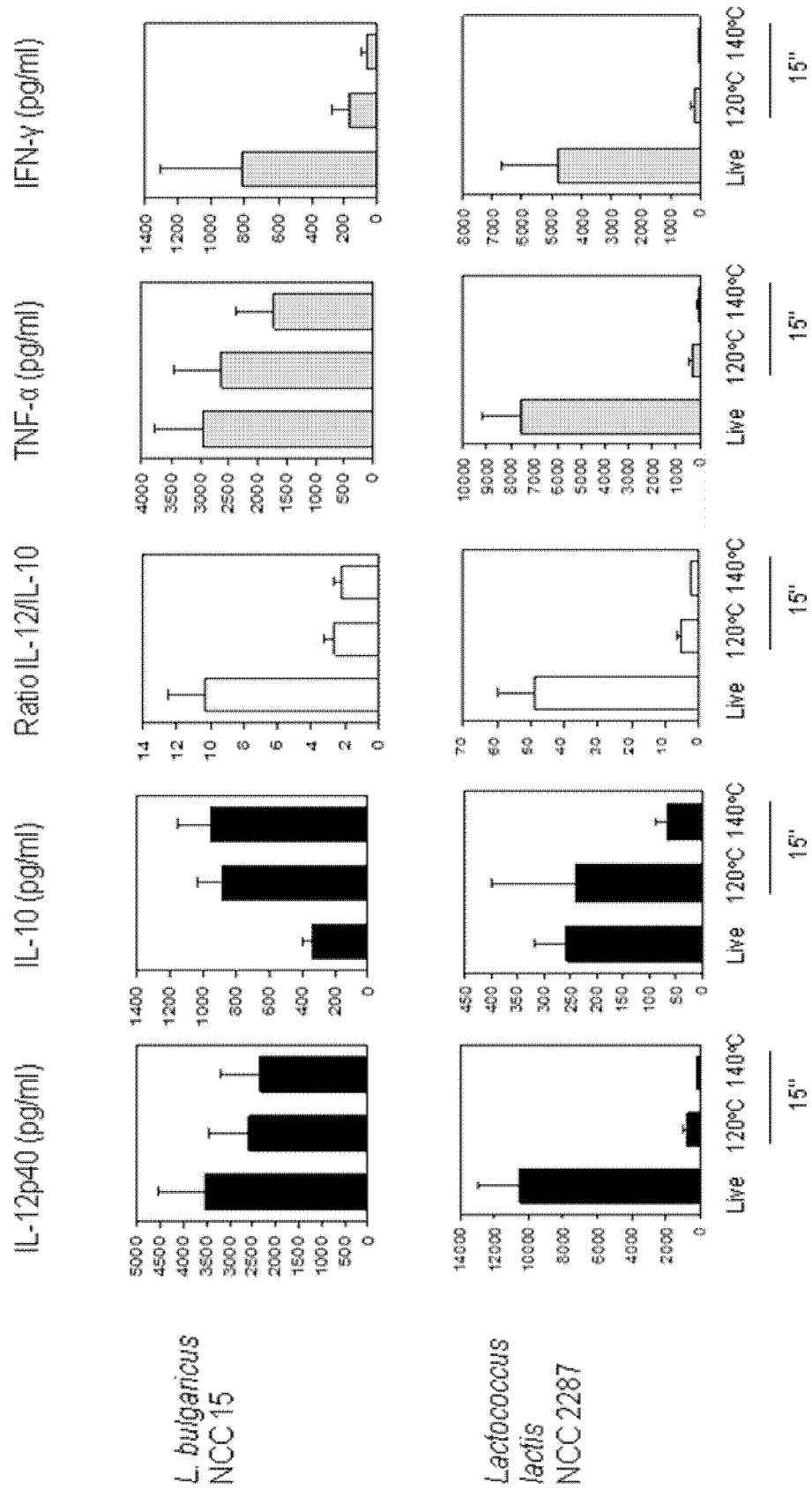
Figure 4B:
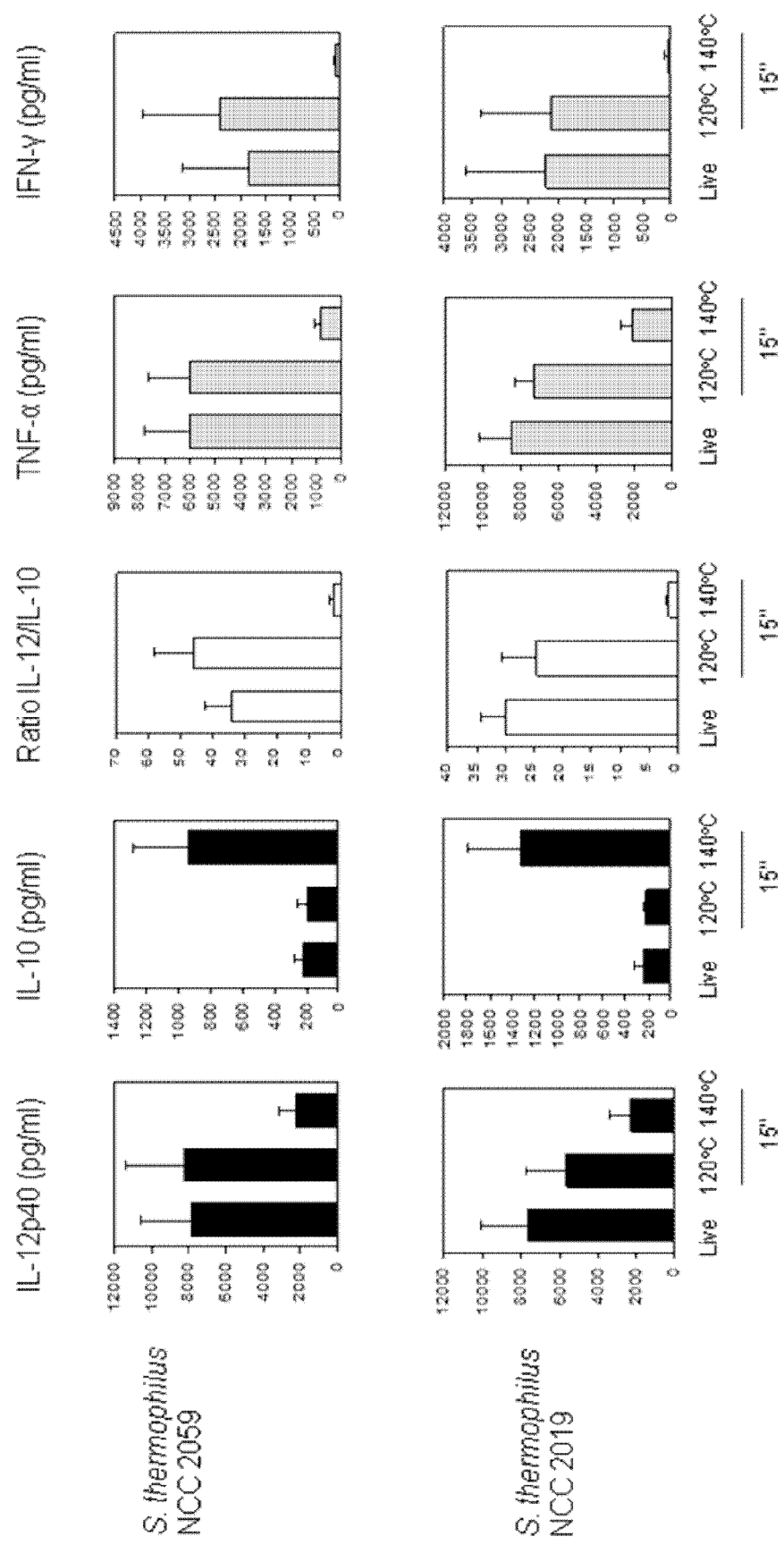
Figure 5:
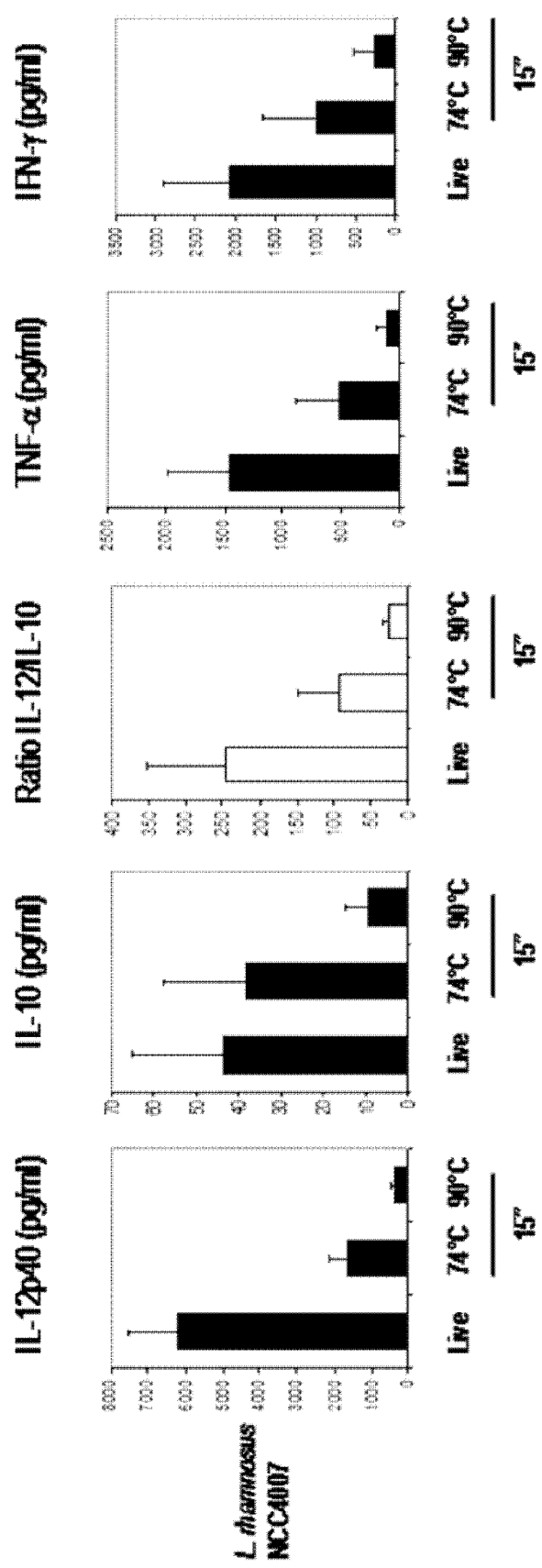
Figure 6:
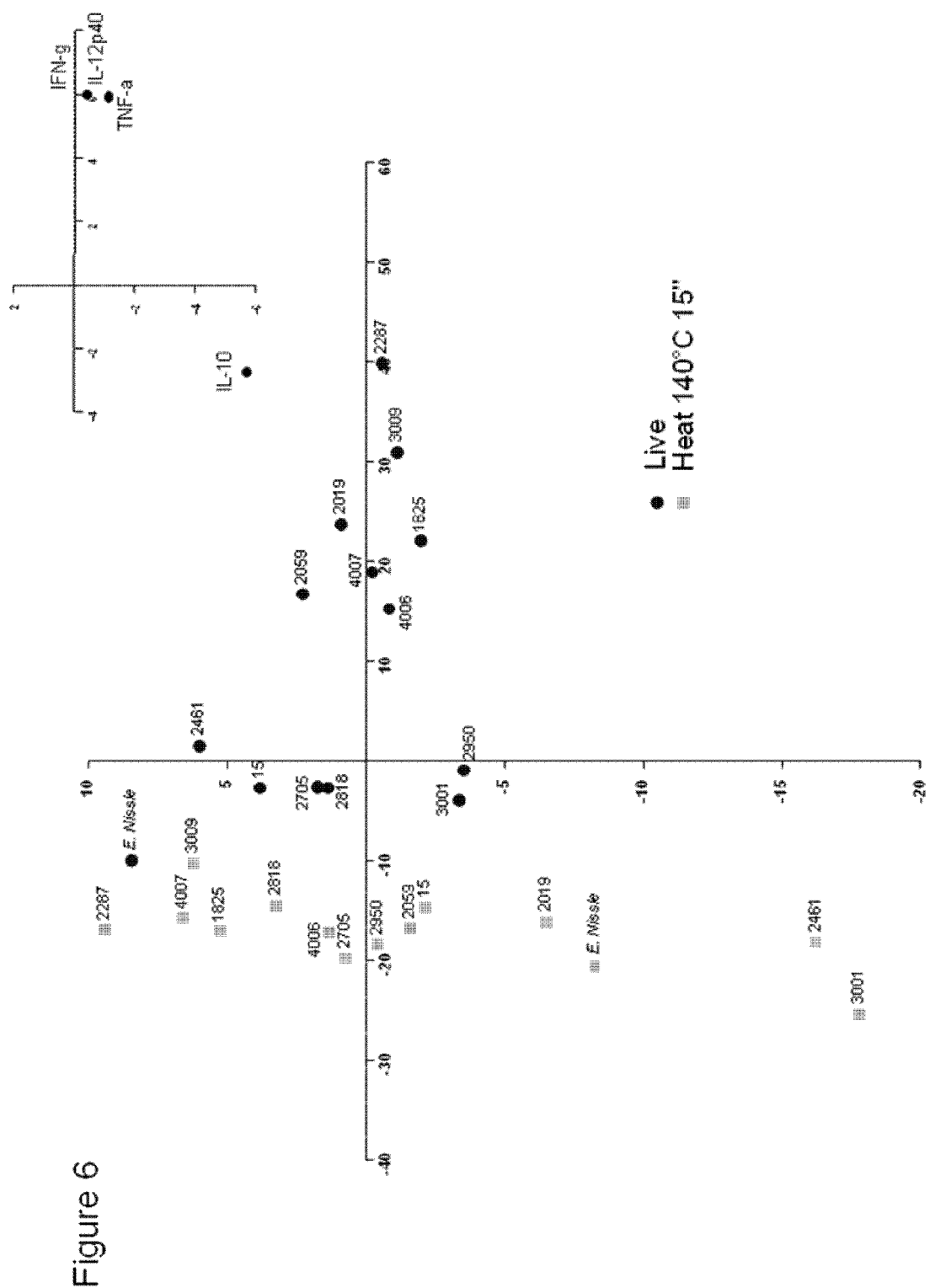
Figure 7:
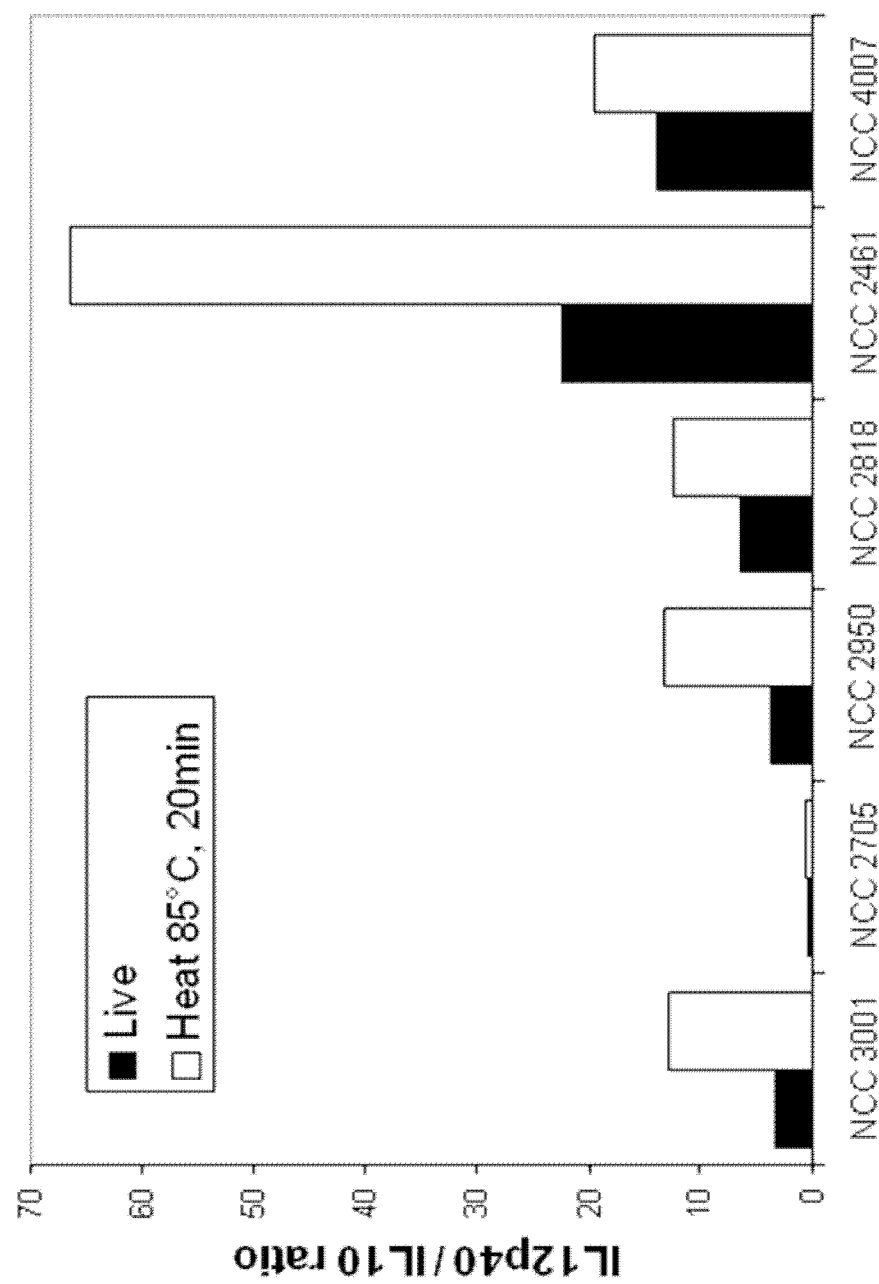
FIG. 7 shows IL-12p40/IL-10 ratios of live and heat treated (85° C., 20 min) strains. Overall, heat treatment at 85° C. for 20 min leads to an increase of IL-12p40/IL-10 ratios as opposed to "short-time high temperature" treatments of the present invention (FIGS. 1, 2, 3, 4 and 5).

Anti-Inflammatory Profiles generated by Ultra High Temperature (UHT)/High Temperature Short Time (HTST)-Like Treatments The probiotic strains under investigation were submitted to a series of heat treatments (Ultra High Temperature (UHT), High Temperature Short Time (HTST) and 85° C. for 20 min) and their immune profiles were compared to those of live cells in vitro. Live micro-organisms (probiotics and/or dairy starter cultures) induced different levels of cytokine production when incubated with human PBMC (FIGS. 1, 2, 3, 4 and 5). Heat treatment of these micro-organisms modified the levels of cytokines produced by PBMC in a temperature dependent manner. "Short-time high temperature" treatments (120° C. or 140° C. for 15") generated non replicating bacteria with anti-inflammatory immune profiles (FIGS. 1, 2, 3 and 4). Indeed, UHT-like treated strains (140° C., 15 sec) induced less pro-inflammatory cytokines (TNF-α, IFN-γ, IL-12p40) while maintaining or inducing additional IL-10 production (compared to live counterparts). The resulting IL-12p40/IL-10 ratios were lower for any UHT-like treated strains compared to live cells (FIGS. 1, 2, 3 and 4). This observation was also valid for bacteria treated by HTST-like treatments, i.e. submitted to 120° C. for 15 sec (FIGS. 1, 2, 3 and 4), or 74° C. and 90° C. for 15 sec (FIG. 5). Heat treatments (UHT-like or HTST-like treatments) had a similar effect on in vitro immune profiles of probiotic strains (FIGS. 1, 2, 3 and 5) and dairy starter cultures (FIG. 4). Principal Component Analysis on PBMC data generated with live and heat treated (140° C., 15") probiotic and dairy starter strains revealed that live strains are spread all along the x axis, illustrating that strains exhibit very different immune profiles in vitro, from low (left side) to high (right side) inducers of pro-inflammatory cytokines. Heat treated strains cluster on the left side of the graph, showing that pro-inflammatory cytokines are much less induced by heat treated strains (FIG. 6). By contrast, bacteria heat treated at 85° C. for 20 min induced more pro-inflammatory cytokines and less IL-10 than live cells resulting in higher IL-12p40/IL-10 ratios (FIG. 7).

Anti-inflammatory profiles are enhanced or generated by UHT-like and HTST-like treatments.

Figure 1A:
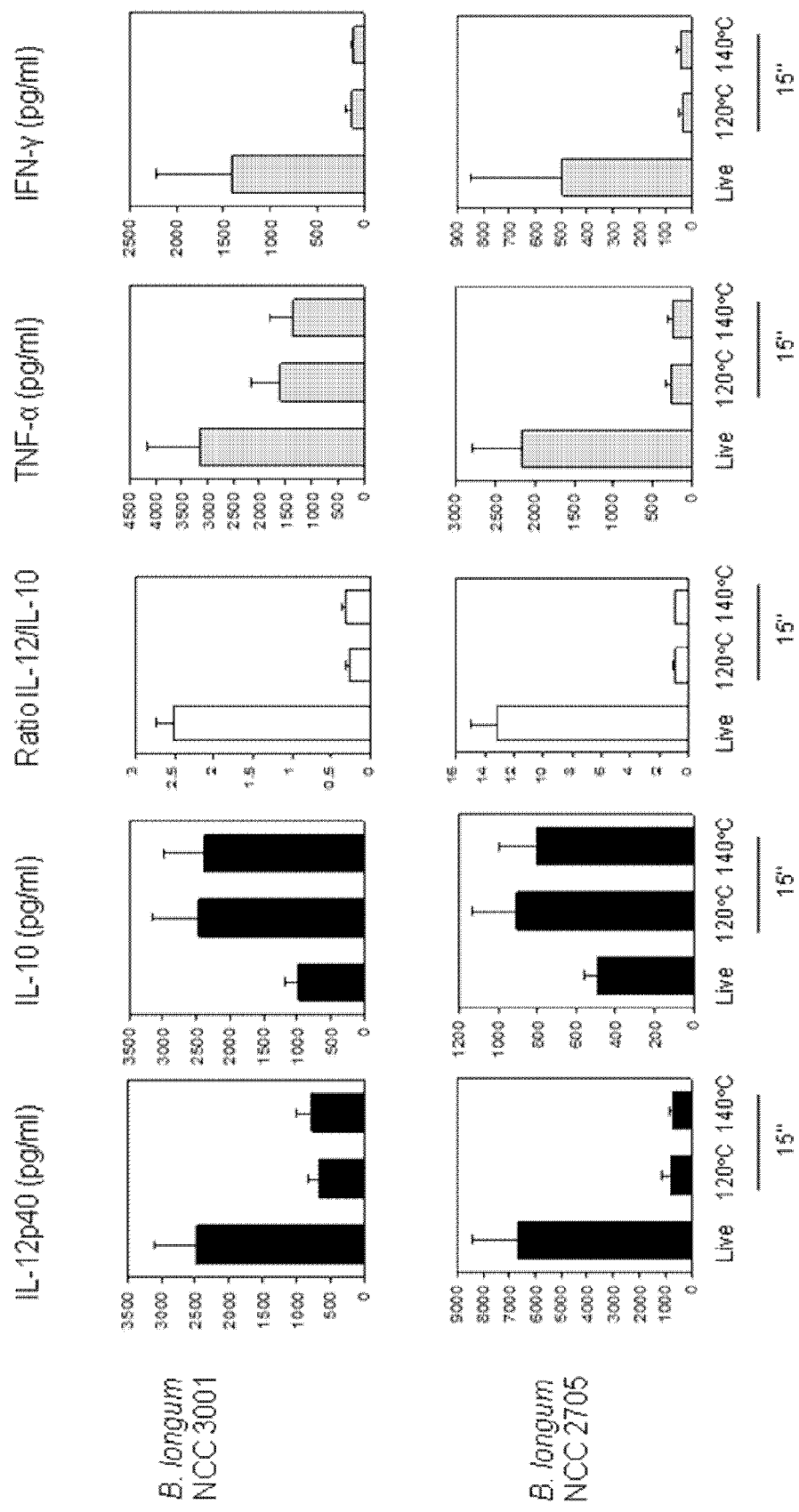
Figure 1B:
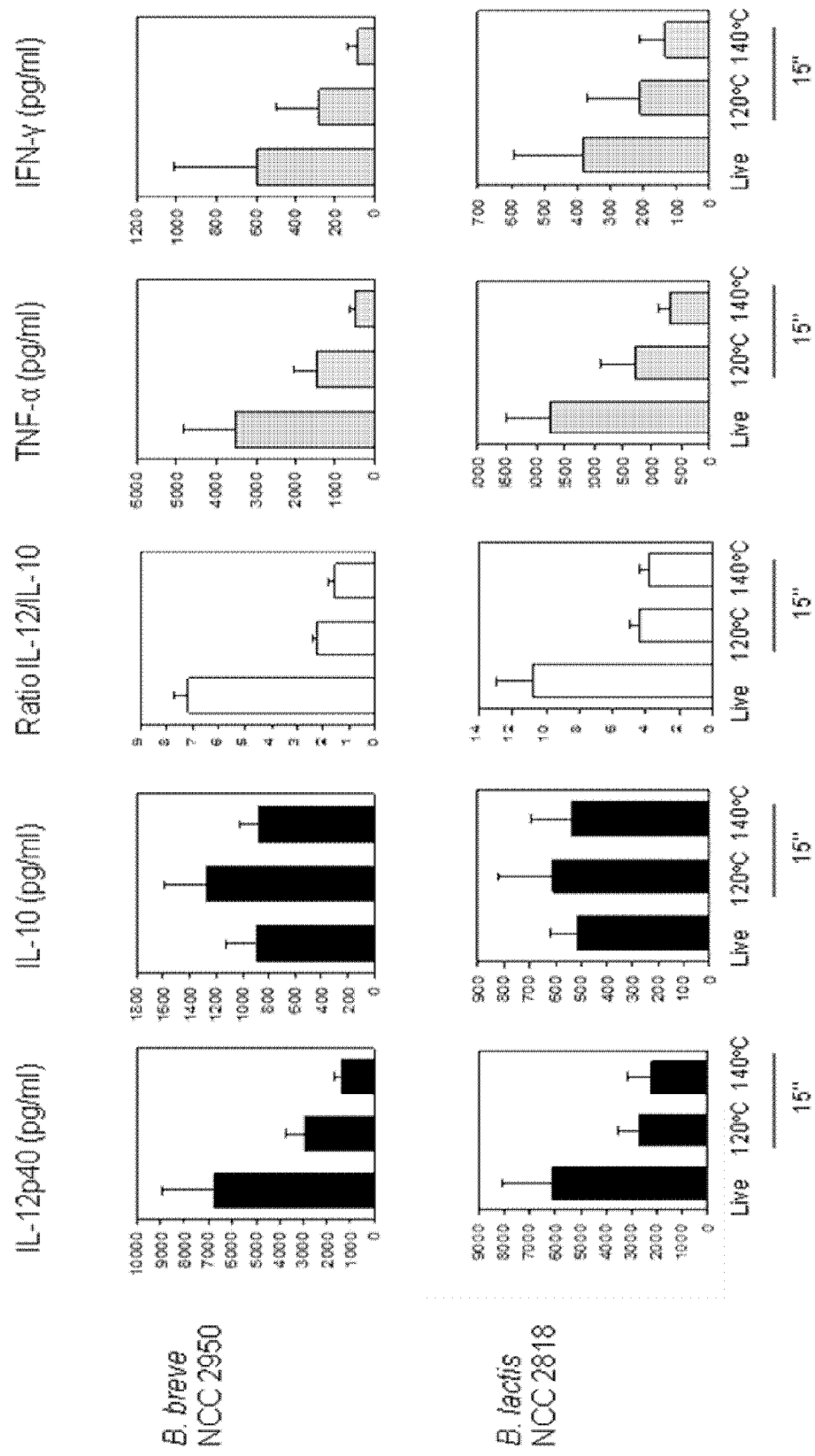
Figure 2:
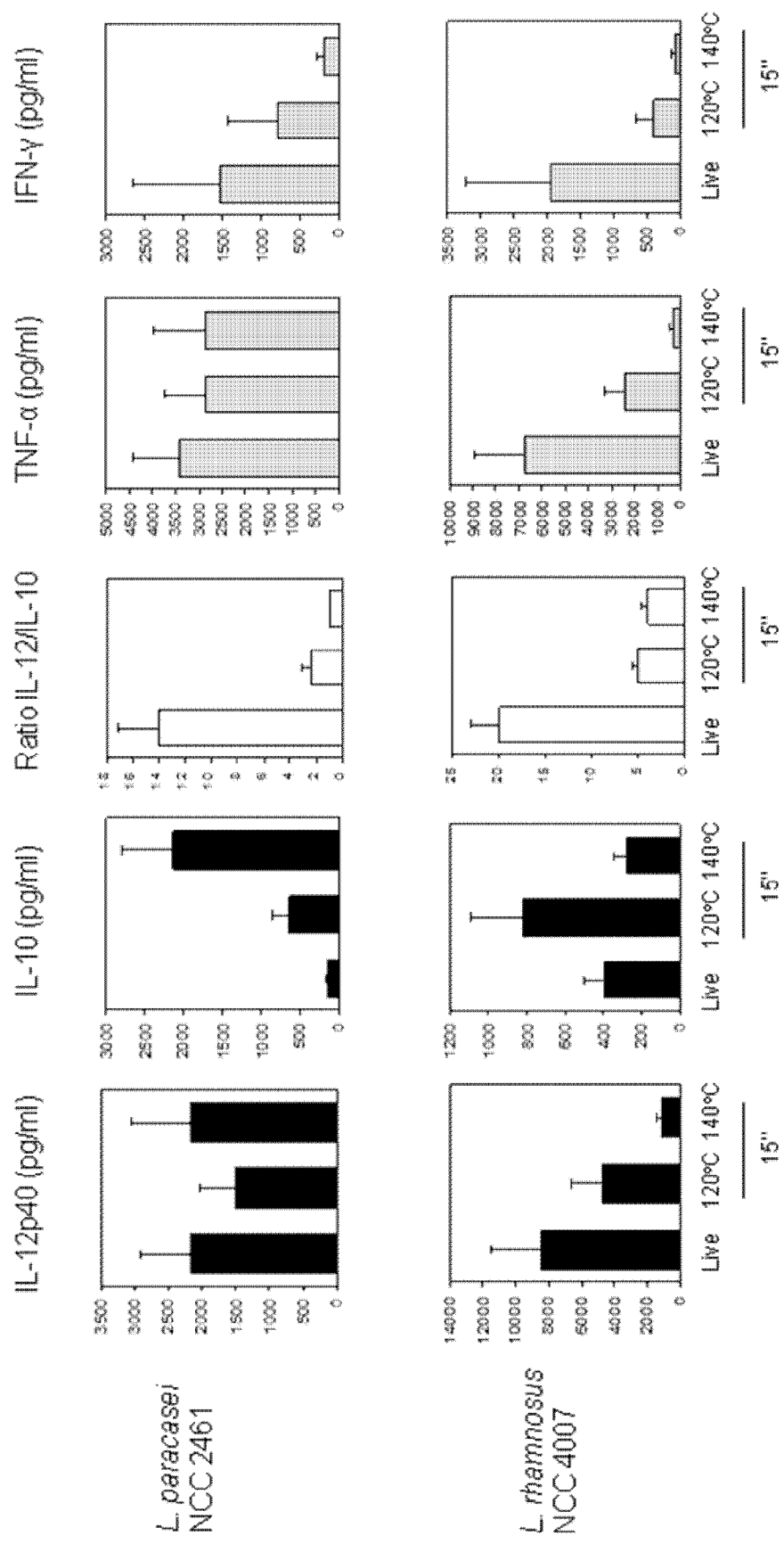
Figure 3A:
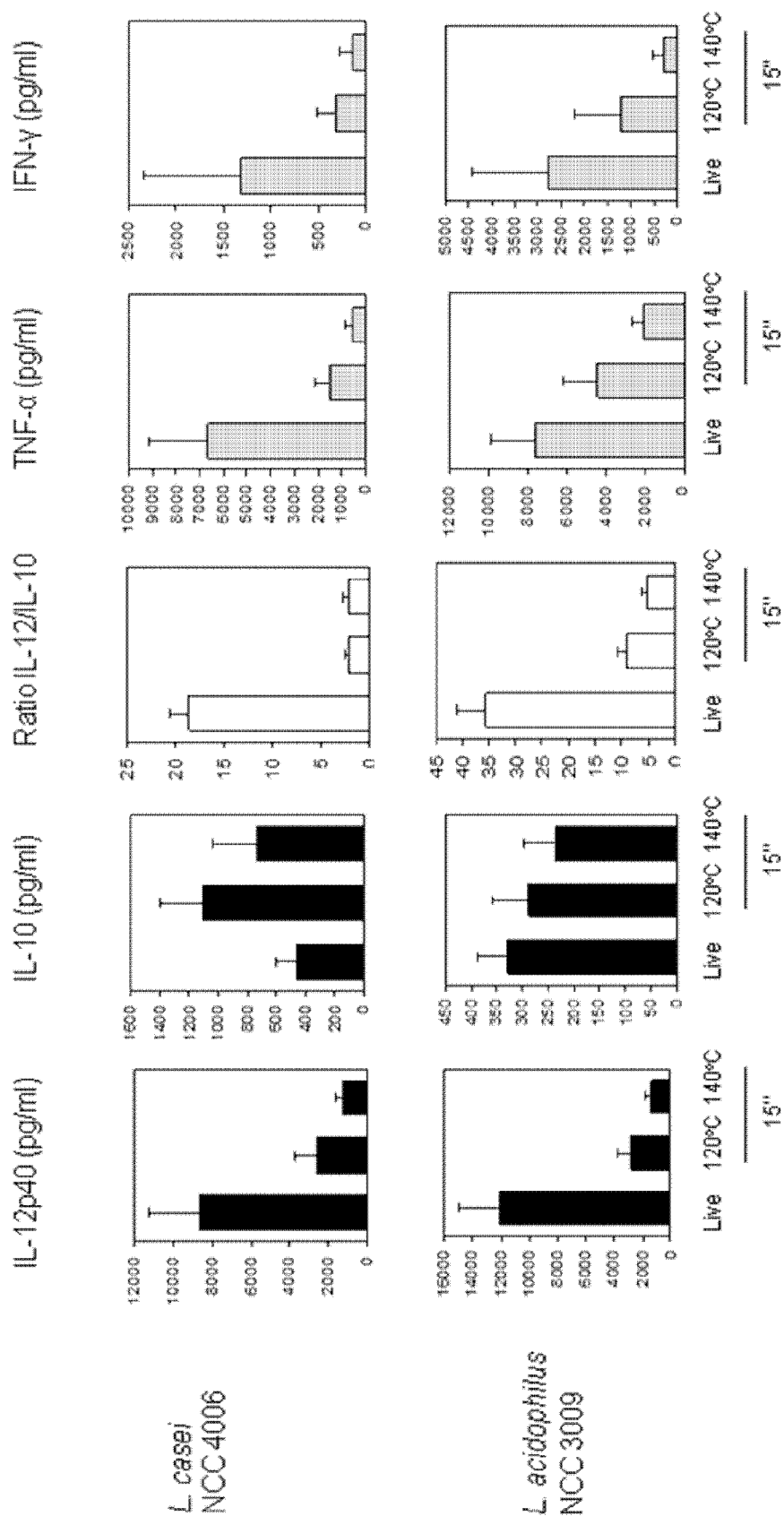
Figure 3B:
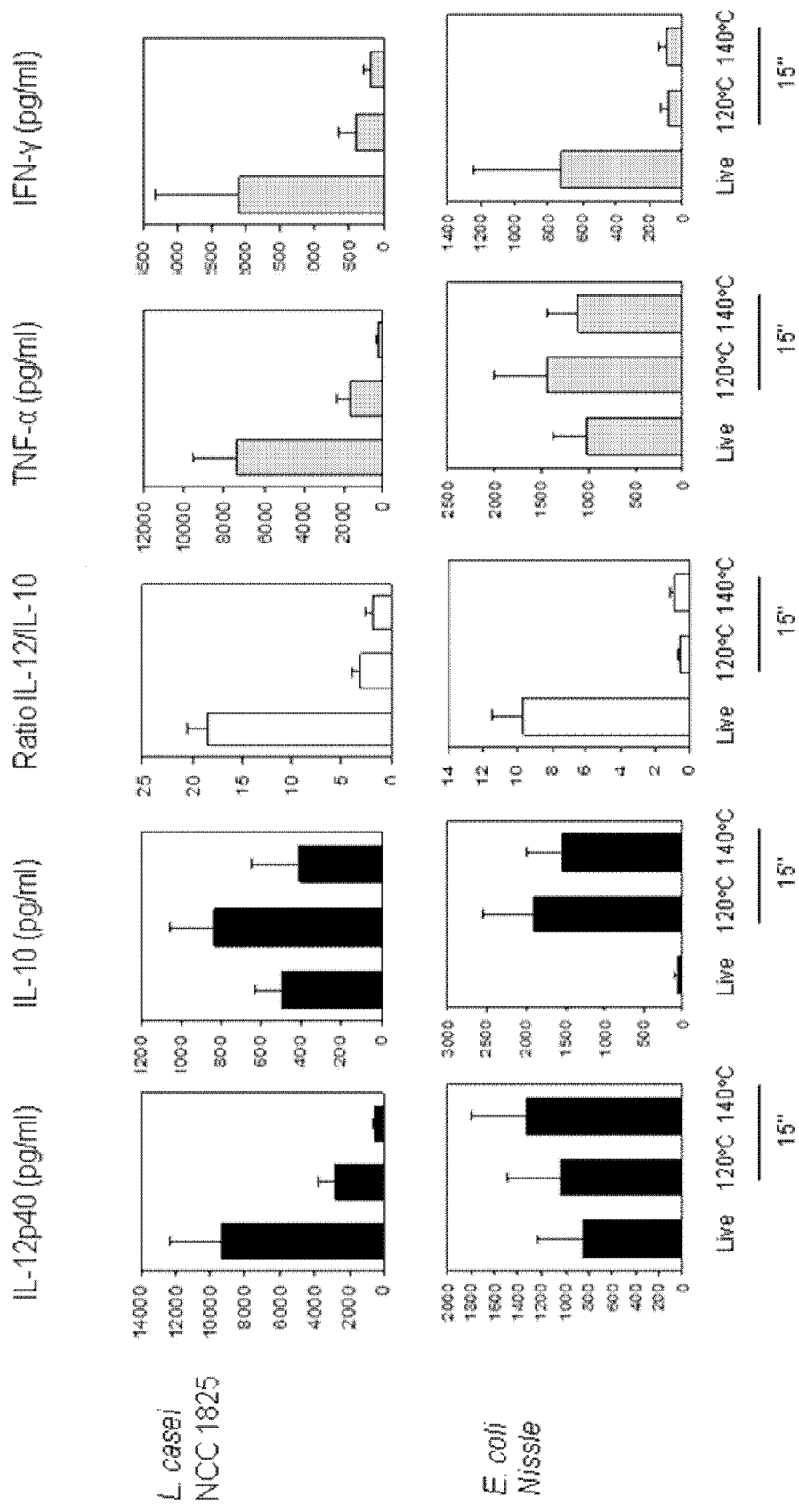

UHT and HTST treated strains exhibit anti-inflammatory profiles regardless of their respective initial immune profiles (live cells). Probiotic strains known to be anti-inflammatory in vivo and exhibiting anti-inflammatory profiles in vitro (*B. longum* NCC 3001, *B. longum* NCC 2705, *B. breve* NCC 2950, *B. lactis* NCC 2818) were shown to exhibit enhanced anti-inflammatory profiles in vitro after "short-time high temperature" treatments. As shown in FIG. 1, the IL-12p40/IL-10 ratios of UHT-like treated *Bifidobacterium* strains were lower than those from the live counterparts, thus showing improved anti-inflammatory profiles of UHT-like treated samples. More strikingly, the generation of anti-inflammatory profiles by UHT-like and HTST-like treatments was also confirmed for non anti-inflammatory live strains. Both live *L. rhamnosus* NCC 4007 and *L. paracasei* NCC 2461 exhibit high IL-12p40/IL-10 ratios in vitro (FIGS. 2 and 5). The two live strains were shown to be not protective against TNBS-induced colitis in mice. The IL-12p40/IL-10 ratios induced by *L. rhamnosus* NCC 4007 and *L. paracasei* NCC 2461 were dramatically reduced after "short-time high temperature" treatments (UHT or HTST) reaching levels as low as those obtained with Bifidobacterium strains. These low IL-12p40/IL-10 ratios are due to low levels of IL-12p40 production combined with no change (L. rhamnosus NCC 4007) or a dramatic induction of IL-10 secretion (L. paracasei NCC 2461) (FIG. 2).

As a consequence:
  Anti-inflammatory profiles of live micro-organisms can be enhanced by UHT-like and HTST-like heat treatments (for instance B. longum NCC 2705, B. longum NCC 3001, B. breve NCC 2950, B. lactis NCC 2818)
  Anti-inflammatory profiles can be generated from non anti-inflammatory live micro-organisms (for example L. rhamnosus NCC 4007, L. paracasei NCC 2461, dairy starters S. thermophilus NCC 2019) by UHT-like and HTST-like heat treatments.
  Anti-inflammatory profiles were also demonstrated for strains isolated from commercially available products (FIGS. 3 A & B) including a probiotic E. coli strain.

The impact of UHT/HTST-like treatments was similar for all tested probiotics and dairy starters, for example lactobacilli, bifidobacteria and streptococci.

UHT/HTST-like treatments were applied to several lactobacilli, bifidobacteria and streptococci exhibiting different in vitro immune profiles. All the strains induced less pro-inflammatory cytokines after UHT/HTST-like treatments than their live counterparts (FIGS. 1, 2, 3, 4, 5 and 6) demonstrating that the effect of UHT/HTST-like treatments on the immune properties of the resulting non replicating bacteria can be generalized to all probiotics, in particular to lactobacilli and bifidobacteria and specific E. coli strains and to all dairy starter cultures in particular to streptococci, lactococci and lactobacilli.

EXAMPLE 2

Methodology

Bacterial Preparations:

Five probiotic strains were used to investigate the immune boosting properties of non-replicating probiotics: 3 bifidobacteria (B. longum NCC3001, B. lactis NCC2818, B. breve NCC2950) and 2 lactobacilli (L. paracasei NCC2461, L. rhamnosus NCC4007).

Bacterial cells were grown on MRS in batch fermentation at 37° C. for 16-18 h without pH control. Bacterial cells were spun down (5,000×g, 4° C.) and resuspended in phosphate buffer saline prior to be diluted in saline water in order to reach a final concentration of around 10E10 cfu/ml. B. longum NCC3001, B. lactis NCC2818, L. paracasei NCC2461, L. rhamnosus NCC4007 were heat treated at 85° C. for 20 min in a water bath. B. breve NCC2950 was heat treated at 90° C. for 30 minutes in a water bath. Heat treated bacterial suspensions were aliquoted and kept frozen at −80° C. until use. Live bacteria were stored at −80° C. in PBS-glycerol 15% until use.

In Vitro Immunoprofiling of Bacterial Preparations

The immune profiles of live and heat treated bacterial preparations (i.e. the capacity to induce secretion of specific cytokines from human blood cells in vitro) were assessed. Human peripheral blood mononuclear cells (PBMCs) were isolated from blood filters. After separation by cell density gradient, mononuclear cells were collected and washed twice with Hank's balanced salt solution. Cells were then resuspended in Iscove's Modified Dulbecco's Medium (IMDM, Sigma) supplemented with 10% foetal calf serum (Biocon-cept, Paris, france), 1% L-glutamine (Sigma), 1% penicillin/streptomycin (Sigma) and 0.1% gentamycin (Sigma). PBMCs ($7 \times 10^5$ cells/well) were then incubated with live and heat treated bacteria (equivalent $7 \times 10^6$ cfu/well) in 48 well plates for 36 h. The effects of live and heat treated bacteria were tested on PBMCs from 8 individual donors splitted into two separate experiments. After 36 h incubation, culture plates were frozen and kept at −20° C. until cytokine measurement. Cytokine profiling was performed in parallel (i.e. in the same experiment on the same batch of PBMCs) for live bacteria and their heat-treated counterparts.

Levels of cytokines (IFN-γ, IL-12p40, TNF-α and IL-10) in cell culture supernatants after 36 h incubation were determined by ELISA (R&D DuoSet Human IL-10, BD OptEIA Human IL12p40, BD OptEIA Human TNF, BD OptEIA Human IFN-γ) following manufacturer's instructions. IFN-γ, IL-12p40 and TNF-α are pro-inflammatory cytokines, whereas IL-10 is a potent anti-inflammatory mediator. Results are expressed as means (pg/ml)+/− SEM of 4 individual donors and are representative of two individual experiments performed with 4 donors each.

In Vivo Effect of Live and Heat Treated Bifidobacterium Breve NCC2950 in Prevention of Allergic Diarrhea A mouse model of allergic diarrhea was used to test the Th1 promoting effect of B. breve NCC2950 (Brandt E. B et al. JCI 2003; 112(11): 1666-1667). Following sensitization (2 intraperitoneal injections of Ovalbumin (OVA) and aluminium potassium sulphate at an interval of 14 days; days 0 and 14) male Balb/c mice were orally challenged with OVA for 6 times (days 27, 29, 32, 34, 36, 39) resulting in transient clinical symptoms (diarrhea) and changes of immune parameters (plasma concentration of total IgE, OVA specific IgE, mouse mast cell protease 1, i.e MMCP-1). Bifidobacterium breve NCC2950 live or heat treated at 90° C. for 30 min, was administered by gavage 4 days prior to OVA sensitization (days −3, −2, −1, 0 and days 11, 12, 13 and 14) and during the challenge period (days 23 to 39). A daily bacterial dose of around $10^9$ colony forming units (cfu) or equivalent cfu/mouse was used.

Results

Induction of Secretion of 'Pro-Inflammatory' Cytokines after Heat Treatment

The ability of heat treated bacterial strains to stimulate cytokine secretion by human peripheral blood mononuclear cells (PBMCs) was assessed in vitro. The immune profiles based on four cytokines upon stimulation of PBMCs by heat treated bacteria were compared to that induced by live bacterial cells in the same in vitro assay.

The heat treated preparations were plated and assessed for the absence of any viable counts. Heat treated bacterial preparations did not produce colonies after plating.

Figure 8:
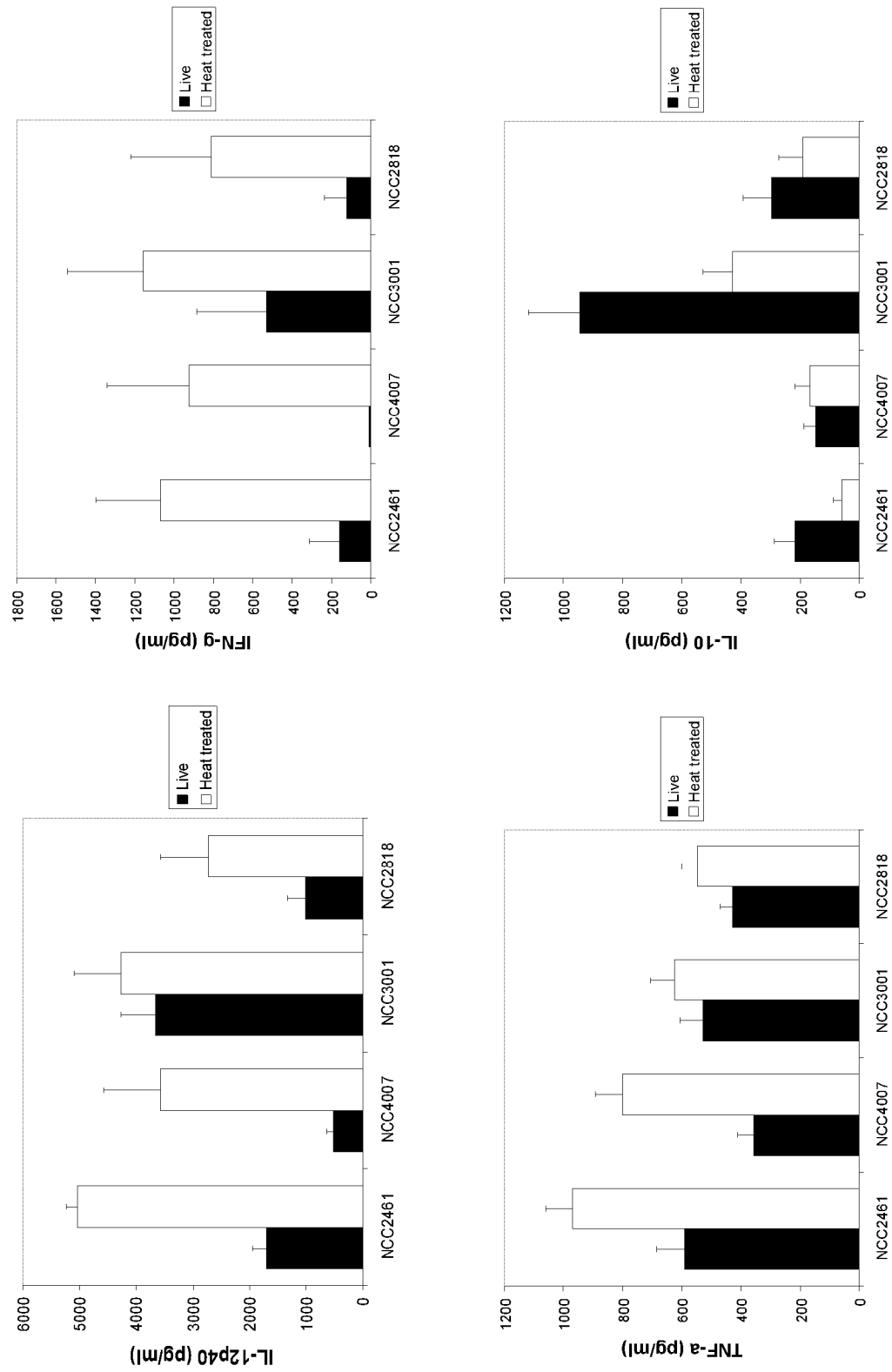
FIG. 8 shows the enhancement of in vitro cytokine secretion from human PBMCs stimulated with heat treated bacteria.

Live probiotics induced different and strain dependent levels of cytokine production when incubated with human PBMCs (FIG. 8). Heat treatment of probiotics modified the levels of cytokines produced by PBMCs as compared to their live counterparts. Heat treated bacteria induced more pro-inflammatory cytokines (TNF-α, IFN-γ, IL-12p40) than their live counterparts do. By contrast heat treated bacteria induced similar or lower amounts of IL-10 compared to live cells (FIG. 8). These data show that heat treated bacteria are more able to stimulate the immune system than their live counterparts and therefore are more able to boost weakened immune defences. In other words the in vitro data illustrate an enhanced immune boost effect of bacterial strains after heat treatment.

In order to illustrate the enhanced effect of heat-treated B. breve NCC2950 (compared to live cells) on the immune system, both live and heat treated *B. breve* NCC2950 (strain A) were tested in an animal model of allergic diarrhea.

As compared to the positive control group, the intensity of diarrhea was significantly and consistently decreased after treatment with heat treated *B. breve* NCC2950 (41.1%±4.8) whereas the intensity of diarrhea was lowered by only 20±28.3% after treatment with live *B. breve* NCC2950. These results demonstrate that heat-treated *B. breve* NCC2950 exhibits an enhanced protective effect against allergic diarrhea than its live counterpart (FIG. 9).

As a consequence, the ability of probiotics to enhance the immune defences was shown to be improved after heat treatment.

EXAMPLE 3

Experimental Protocol

T84 cells were used from passage 30-40 and cultured in Dulbecco's modified essential medium/F-12 (Sigma D 6421) containing 5% of foetal calf serum (FCS) (Amined BioConcept) and 2 mM glutamine. Cells were seeded at a concentration of $2\times10^6$ cell/well in 6-well culture plates and grown as monolayers at 37° C. in a 5% $CO_2$-95% air atmosphere. Cells grown to 1 week after confluence were incubated with serum and antibiotic-free medium for at least 12H. This step was necessary to eliminate serum-induced defensin expression and prevent any influence of antibiotics on the probiotics and on the cell immune response. Cells were further incubated with probiotics or heat-treated strains for 4H. At the end of the incubation time, cells were washed with PBS and harvested with TriPure™ isolation reagent according to the supplier's protocol. Human hBD1 and hBD2 gene expression in the so-treated cells was assessed by quantitative PCR.

Bacterial strains used in this experiment are *B. longum* (NCC 2705, deposit number CNCM I-2618), *B. lactis* (NCC 2818, deposit number CNCM I-3446), *L. johnsonii* (La1, NCC 533, deposit number CNCM I-1225), *L. paracasei* (ST11, NCC 2461, deposit number CNCM I-2116). These strains were tested live or heat-treated at either 120° C.-15 sec or 85° C.-20 min.

Results:

Heat-treated La1 (NCC533, deposit number CNCM I-1225) at 120° C., 15 sec induced strongly hBD1 mRNA expression after 4 h of incubation (FIG. 10) in contrast to the other tested heat-treated strains. These data are unique, as HBD1 expression, which is constituvely expressed, is currently thought by the scientific community as virtually non modulable by microbes, microbial products or inflammation.

Both live and heat-treated La1 (NCC533, deposit number CNCM I-1225) strongly induced hBD1 mRNA expression, but the highest induction of hBD1 was elicited by heat-treated La1 (high temperature and short time treatment) (FIG. 11).

The invention claimed is:

1. A method for treatment of gastrointestinal infections in children comprising administering to a child in need of same a therapeutically-effective amount of a composition comprising non-replicating probiotic micro-organisms that have been rendered non-replicating by a heat treatment at a temperature of 120° C. to 140° C. for 5-15 seconds, wherein the probiotic micro-organisms are selected from the group consisting of Bifidobacteria, Lactobacilli, Propionibacteria, and combinations thereof, and the composition is administered in an amount to provide about 0.005 mg-1000 mg of the non-replicating micro-organisms to the child per day.

2. The method of claim 1, wherein the gastrointestinal infection results in diarrhea.

3. The method of claim 1 comprising the step of strengthening a child's ability to fight gastrointestinal infections by administering the composition.

4. The method of claim 1 comprising the step of reducing the time a gastrointestinal infection will last by administering the composition.

5. The method of claim 1 comprising the step of helping children to recover from gastrointestinal infections faster by administering the composition.

6. The method of claim 1 comprising the step of helping children to get gastrointestinal infections less often by administering the composition.

7. The method of claim 1, wherein the composition comprises about $10^6$ to $10^{12}$ cfu of the non-replicating probiotic micro-organisms.

8. The method claim 1, wherein the heat treatment is performed at a temperature exceeding 135° C., and the non-replicating probiotic micro-organisms are selected from the group consisting of *Lactobacillus paracasei* NCC 2461, *Lactobacillus rhamnosus* NCC 4007, and combinations thereof.

9. The method of claim 1, wherein the composition comprises probiotics, and at least 90% of the probiotics are the non-replicating probiotic micro-organisms.

10. The method of claim 1, wherein the non-replicating probiotic micro-organisms are selected from the group consisting of *Bifidobacterium longum, Bifidobacterium lactis, Bifidobacterium animalis, Bifidobacterium breve, Bifidobacterium infantis, Bifidobacterium adolescentis, Lactobacillus acidophilus, Lactobacillus casei, Lactobacillus paracasei, Lactobacillus salivarius, Lactobacillus reuteri, Lactobacillus rhamnosus, Lactobacillus johnsonii, Lactobacillus plantarum, Lactobacillus fermentum, Lactococcus lactis, Lactobacillus bulgaricus, Lactobacillus helveticus, Lactobacillus delbrueckii*, and mixtures thereof.

11. The method of claim 1, wherein the non-replicating probiotic micro-organisms are selected from the group consisting of *Bifidobacterium longum* NCC 2705 (CNCM I-2618), *Bifidobacterium breve* NCC 2950 (CNCM I-3865), *Bifidobacterium lactis* NCC 2818 (CNCM I-3446), *Lactobacillus johnsonii* La1 (CNCM I-1225), *Lactobacillus paracasei* NCC 2461 (CNCM I-2116), *Lactobacillus* rhamnosus NCC 4007 (CGMCC 1.3724), *Lactobacillus reuteri* DSM17938, *Lactobacillus reuteri* ATCC55730, *Lactobacillus acidophilus* NCC 3009 (ATCC 700396), *Lactobacillus casei* ACA-DC 6002 (NCC 1825), and combinations thereof.

12. The method of claim 1, wherein the non-replicating probiotic micro-organisms are selected from the group consisting of *Lactobacillus bulgaricus* CNCM I-1198, *Bifidobacterium longum* ATCC BAA-999, and combinations thereof.

\* \* \* \* \*